United States Patent
Aeschlimann et al.

(10) Patent No.: US 9,801,673 B2
(45) Date of Patent: Oct. 31, 2017

(54) IMPLANT, IMPLANTATION DEVICE, IMPLANTATION METHOD

(71) Applicant: Woodwelding AG, Stansstad (CH)

(72) Inventors: Marcel Aeschlimann, Ligerz (CH);
Laurent Torriani, Lamboing (CH);
Mario Lehmann, Les Pommerats (CH);
Jörg Mayer, Niederlenz (CH)

(73) Assignee: WOODWELDING AG, Stansstad (CH)

( * ) Notice: Subject to any disclaimer, the term of this patent is extended or adjusted under 35 U.S.C. 154(b) by 0 days.

(21) Appl. No.: 15/251,442

(22) Filed: Aug. 30, 2016

(65) Prior Publication Data

US 2016/0367302 A1    Dec. 22, 2016

Related U.S. Application Data

(60) Continuation of application No. 14/492,521, filed on Sep. 22, 2014, now Pat. No. 9,445,888, which is a
(Continued)

(51) Int. Cl.
*A61B 17/86* (2006.01)
*A61B 17/84* (2006.01)
(Continued)

(52) U.S. Cl.
CPC ........ *A61B 17/844* (2013.01); *A61B 17/0401* (2013.01); *A61B 17/68* (2013.01); *A61B 17/686* (2013.01); *A61B 17/8872* (2013.01); *A61C 8/0016* (2013.01); *A61F 2/0811* (2013.01); *A61F 2/3601* (2013.01); *A61F 2/3609* (2013.01); *A61B 17/8822* (2013.01); *A61B 2017/00004* (2013.01); *A61B 2017/042* (2013.01); *A61B 2017/0403* (2013.01); *A61B 2017/0424* (2013.01); *A61C 8/0012* (2013.01); (Continued)

(58) Field of Classification Search
CPC ........................... A61B 17/844; A61B 17/686
USPC .......................................... 606/232, 300–321
See application file for complete search history.

(56) References Cited

U.S. PATENT DOCUMENTS 3,846,846 A    11/1974   Fischer
4,447,915 A *   5/1984   Weber ................. A61F 2/30723
                                                    606/95
(Continued)

FOREIGN PATENT DOCUMENTS

CH          655650 A2    5/1986
EP          0597553 A1   5/1994
(Continued)

*Primary Examiner* — Matthew Lawson
(74) *Attorney, Agent, or Firm* — Rankin, Hill & Clark LLP

(57) ABSTRACT

An implant suitable for being anchored with the aid of mechanical vibration in an opening provided in bone tissue. The implant is compressible in the direction of a compression axis under local enlargement of a distance between a peripheral implant surface and the compression axis. The implant includes a coupling-in face which serves for coupling a compressing force and the mechanical vibrations into the implant, which coupling-in face is not parallel to the compression axis. The implant also includes a thermoplastic material which, in areas of the local distance enlargement, forms at least a part of the peripheral surface of the implant.

13 Claims, 10 Drawing Sheets

Related U.S. Application Data division of application No. 11/858,457, filed on Sep. 20, 2007, now Pat. No. 8,870,933.

(60) Provisional application No. 60/826,300, filed on Sep. 20, 2006.

(51) Int. Cl.

| | | |
|---|---|---|
| *A61B 17/04* | (2006.01) | |
| *A61B 17/68* | (2006.01) | |
| *A61F 2/08* | (2006.01) | |
| *A61F 2/36* | (2006.01) | |
| *A61B 17/88* | (2006.01) | |
| *A61B 17/00* | (2006.01) | |
| *A61C 8/00* | (2006.01) | |
| *A61F 2/28* | (2006.01) | |
| *A61F 2/30* | (2006.01) | |
| *A61F 2/46* | (2006.01) | |

(52) U.S. Cl.
CPC ........... *A61C 8/0018* (2013.01); *A61F 2/2875* (2013.01); *A61F 2/30749* (2013.01); *A61F 2/4603* (2013.01); *A61F 2002/0835* (2013.01); *A61F 2002/0888* (2013.01); *A61F 2002/3021* (2013.01); *A61F 2002/3023* (2013.01); *A61F 2002/3052* (2013.01); *A61F 2002/30065* (2013.01); *A61F 2002/30136* (2013.01); *A61F 2002/30143* (2013.01); *A61F 2002/30205* (2013.01); *A61F 2002/30217* (2013.01); *A61F 2002/30235* (2013.01); *A61F 2002/30309* (2013.01); *A61F 2002/30332* (2013.01); *A61F 2002/30377* (2013.01); *A61F 2002/30405* (2013.01); *A61F 2002/30457* (2013.01); *A61F 2002/30561* (2013.01); *A61F 2002/30579* (2013.01); *A61F 2002/30599* (2013.01); *A61F 2002/30604* (2013.01); *A61F 2002/30904* (2013.01); *A61F 2002/30973* (2013.01); *A61F 2002/365* (2013.01); *A61F 2002/3611* (2013.01); *A61F 2002/3625* (2013.01); *A61F 2002/4683* (2013.01); *A61F 2210/0071* (2013.01); *A61F 2220/0008* (2013.01); *A61F 2220/0016* (2013.01); *A61F 2220/0025* (2013.01); *A61F 2220/0033* (2013.01); *A61F 2220/0058* (2013.01); *A61F 2230/0004* (2013.01); *A61F 2230/0017* (2013.01); *A61F 2230/0063* (2013.01); *A61F 2230/0067* (2013.01); *A61F 2230/0069* (2013.01); *A61F 2250/0063* (2013.01)

(56) References Cited

U.S. PATENT DOCUMENTS

| | | | |
|---|---|---|---|
| 5,593,425 | A | 1/1997 | Bonutti et al. |
| 5,993,458 | A | 11/1999 | Vaitekunas et al. |
| 6,669,733 | B1 | 12/2003 | Spierings |
| 6,913,666 | B1* | 7/2005 | Aeschlimann ...... B29C 66/7392 156/303.1 |
| 6,921,264 | B2 | 7/2005 | Mayer et al. |
| 7,329,263 | B2 | 2/2008 | Bonutti et al. |
| 7,335,205 | B2 | 2/2008 | Aeschlimann et al. |
| 7,950,129 | B2* | 5/2011 | Clinch .............. B29C 66/43421 29/505 |
| 2002/0183851 | A1 | 12/2002 | Spiegelberg et al. |
| 2004/0030341 | A1* | 2/2004 | Aeschlimann ... A61B 17/00491 606/232 |
| 2004/0038180 | A1* | 2/2004 | Mayer .................. A61B 17/68 433/173 |
| 2004/0053196 | A1 | 3/2004 | Mayer et al. |
| 2005/0222575 | A1 | 10/2005 | Ciccone et al. |
| 2006/0105295 | A1 | 5/2006 | Mayer et al. |
| 2007/0270833 | A1* | 11/2007 | Bonutti .............. A61B 17/0401 606/28 |
| 2008/0021474 | A1 | 1/2008 | Bonutti et al. |
| 2008/0039845 | A1 | 2/2008 | Bonutti et al. |
| 2009/0018560 | A1* | 1/2009 | Mayer ...................... A61F 2/30 606/151 |
| 2009/0024161 | A1 | 1/2009 | Bonutti et al. |
| 2010/0211120 | A1 | 8/2010 | Bonutti et al. |

FOREIGN PATENT DOCUMENTS

| | | |
|---|---|---|
| GB | 2253564 A | 9/1992 |
| GB | 2324731 A | 11/1998 |
| WO | 00/79137 | 12/2000 |
| WO | 01/66045 | 9/2001 |
| WO | 02/069817 | 9/2002 |
| WO | 03/046390 | 6/2003 |
| WO | 2004/017857 | 3/2004 |
| WO | 2005/079696 | 9/2005 |
| WO | 2005/105208 | 11/2005 |
| WO | 2008/116203 | 9/2008 |

\* cited by examiner

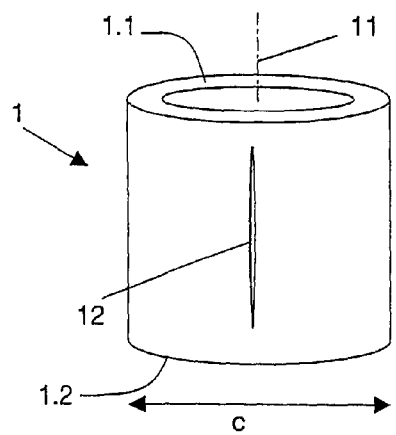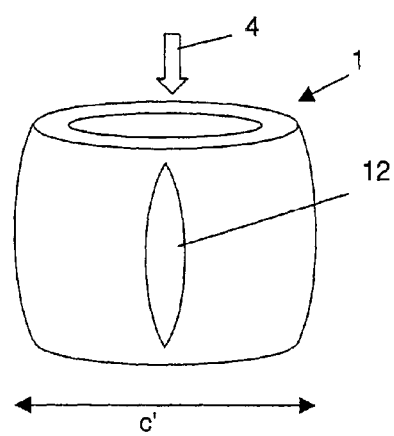
Fig. 1a    Fig. 1b
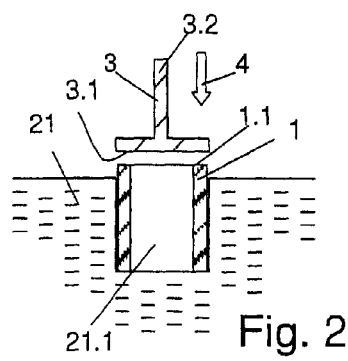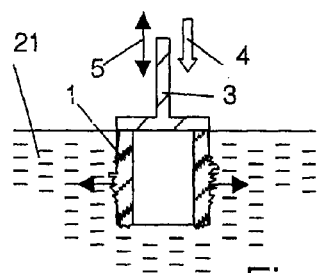
Fig. 2a    Fig. 2b
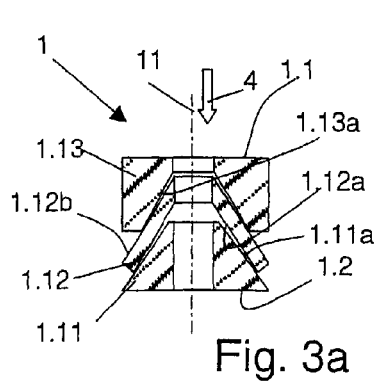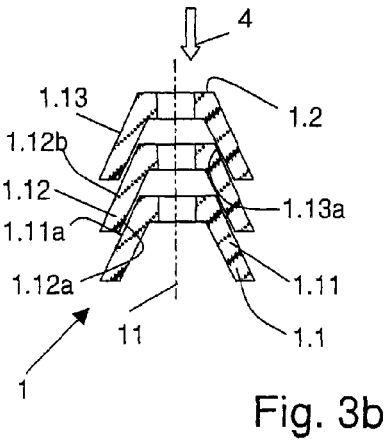
Fig. 3a    Fig. 3b

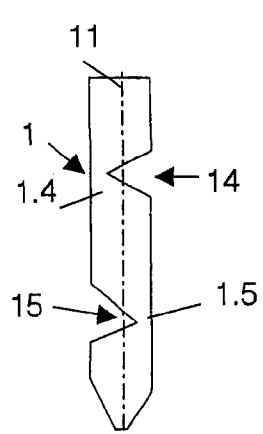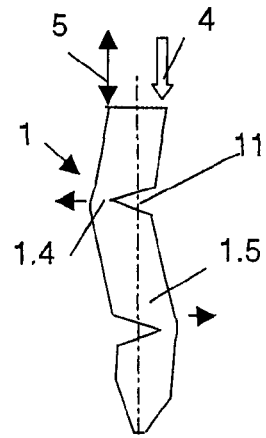
Fig. 8a  Fig. 8b
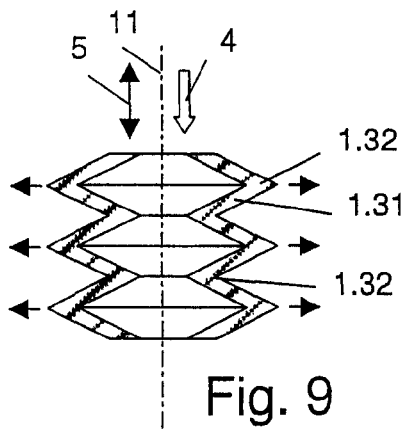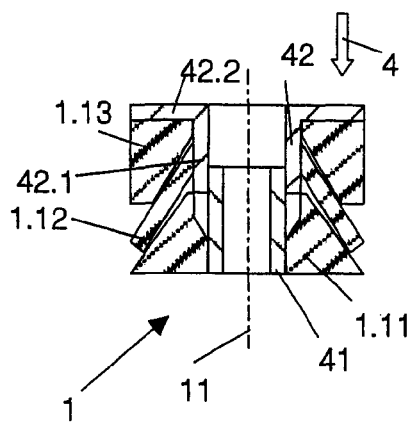
Fig. 9  Fig. 10
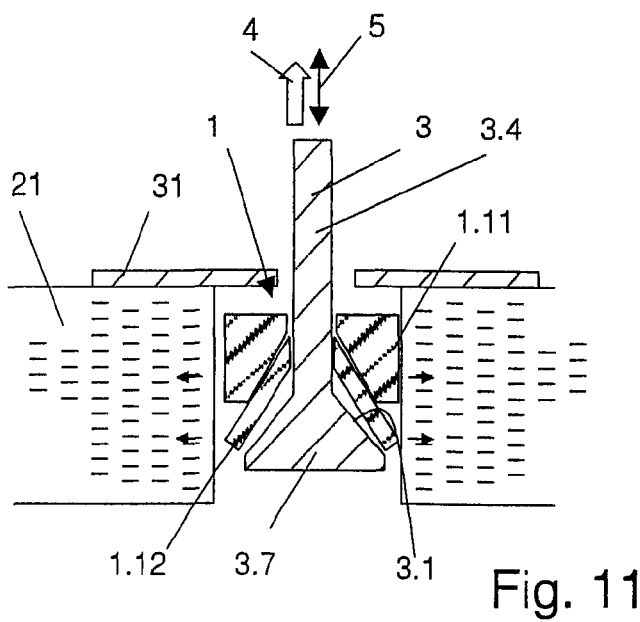
Fig. 11

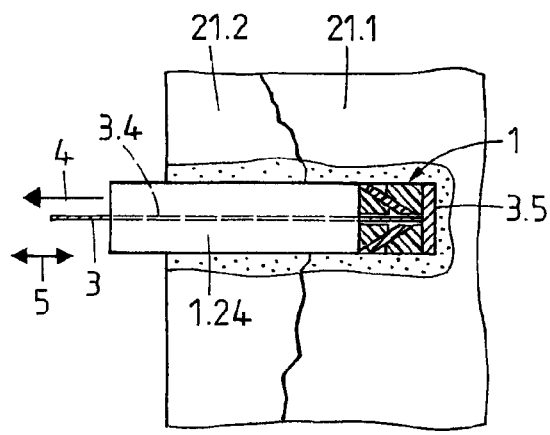
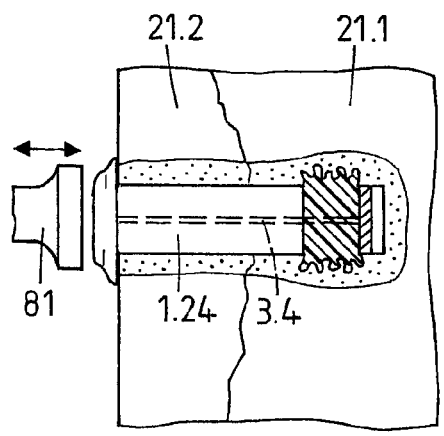
Fig. 25a  Fig. 25b
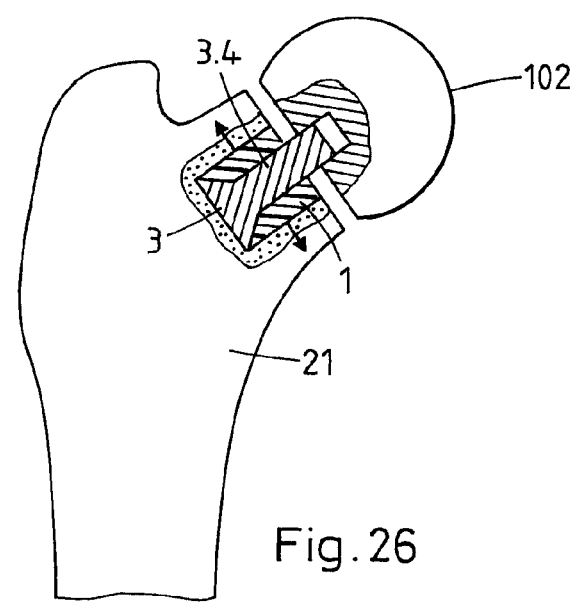
Fig. 26

IMPLANT, IMPLANTATION DEVICE, IMPLANTATION METHOD

BACKGROUND OF THE INVENTION

The invention lies in the field of medical technology and concerns implants, surgical devices, and surgical methods. It especially concerns implants suitable for being anchored in hard tissue, in particular in bone tissue, with the aid of mechanical vibrations, through which a, for example, thermoplastic material provided on the implant is liquefied in places where it is in contact with the hard tissue.

Such implants and corresponding methods for anchoring these in bone tissue are known from the publications WO 02/069 817, WO 2004/017 857 and WO 2005/079 696. The thermoplastic material of such implants is liquefied by mechanical vibrations while being pressed against osseous material, so that it is pressed into cavities (pores, artificially produced cavities) of the osseous material. This results in a most effective anchoring of the implant in bone tissue.

There are situations however, in which anchoring of implants in hard tissue by mechanical vibrations according to the state-of-the-art technology does not suffice or in which, for technical, anatomical or physiological reasons, it is not possible to load a known implant with sufficient vibratory energy to ensure a reliable anchoring by the known methods.

It is therefore the object of the invention to provide implants suitable for being anchored in bone tissue under conditions, which hitherto made such implantations impossible or extremely difficult. It is also the object of the invention to provide methods of anchoring implants, which permit an implantation under conditions, which hitherto made such implantations impossible or extremely difficult.

BRIEF SUMMARY OF THE INVENTION

A first aspect of the invention provides an implant suitable for being anchored in an opening in bone tissue with the aid of mechanical vibration. The implant is able to be compressed in the direction of a chosen compression axis with the effect of a local enlargement of a distance between a peripheral implant surface and the compression axis (measured at right angles to the compression axis). The implant comprises a coupling-in face for the coupling of a compressing force and of the mechanical vibration into the implant, and a thermoplastic material, which forms at least a part of the implant surface in the region of the aforementioned distance enlargement.

A corresponding method of implanting such an implant in bone tissue contains the following steps:
providing an opening in the bone tissue;
positioning the implant in the opening so that the compression axis extends essentially parallel with an opening axis;
coupling a compressing force and mechanical vibrations via the coupling-in face into the positioned implant, thereby causing the implant to be compressed and, due to the distance enlargement, to be pressed at least locally against the side walls of the opening and therewith causing the thermoplastic material to liquefy at least partly where it is in contact with the side walls and to be pressed into the structures of the bone tissue, in order to form a form-fit connection after re-solidification.

The methods and implants described in this text are suitable for implanting an implant in bone tissue, as well as in other hard tissue (especially dentine), and in bone tissue or other hard tissue replacement material. For reasons of simplicity, the following text mostly mentions bone tissue—meaning preferably live bone tissue, this includes the possibility of performing steps of a surgical operation ex situ. However, the teaching of this text also applies to other hard tissues and to hard tissue replacement material.

In the present text the term "implant" is used for describing an artificially produced element, which is brought into the body and either remains there permanently, is resorbed there, or is removed after a certain period. On one hand, the term "implant" is used in particular for elements suitable for connecting two parts of the skeleton, or between one part of the skeleton and a soft tissue part, or between at least one part of the skeleton and another object; this also includes implants used in dental surgery such as the classic dental implants. On the other hand, the term is also used for describing endoprostheses such as e.g. joint prostheses, bone prostheses, intervertebral disc prostheses, artificial ligaments or tendons, artificial teeth, endodontic posts, etc.

In this text "thermoplastic material" is used for describing a material comprising at least one thermoplastic component able to be liquefied by mechanical vibrations while in contact with a hard surface. The frequency of the mechanical vibrations often lies between 2 kHz and 200 kHz and their amplitudes are around 10 μm, i.e. between 1 μm and 100 μm. If the thermoplastic material is to take over a load bearing function and is to liquefy only in the named contact areas—corresponding embodiments are described below—it ought to have an elasticity coefficient of more than 0.5 GPa and a plastification temperature of up to 200° C., of between 200° C. and 300° C. or of more than 300° C. Depending on the application, the thermoplastic material may or may not be resorbable.

Suitable non-resorbable thermoplastic materials are, each of medical quality, polyolefines (e.g. polyethylene), polyacrylates, polymethacrylates, polycarbonates, polyamides, polyesters, polyurethanes, polysulfones, liquid crystal polymers (LCPs), polyacetals, halogenated polymers, in particular halogenated polyolefines, polyphenylene sulphones, polysulfones, polyarylether ketones (e.g. polyether etherketone PEEK), polyethers, or corresponding copolymers and/or blended polymers and/or composites of such polymers, in particular polyamide 11 or polyamide 12.

Suitable resorbable thermoplastic materials are, each of medical quality, thermoplastic polymers based on lactic and/or glycolic acid (PLA, PLLA, PGA, PLGA etc.) or polyhydroxy-alkanoates (PHA), polycaprolactones (PCL), polysaccharides, polydioxanons (PD), polyanhydrides, polypeptides, trimethyl-carbonates (TMC), or corresponding copolymers and/or blended polymers and/or composites of such polymers. Especially suitable as resorbable thermoplastic materials are poly-LDL-lactides (e.g. available from Böhringer under the commercial name Resomer LR706) or poly-DL-lactides (e.g. available from Böhringer under the commercial name Resomer R208).

Returning to the first aspect of the invention, in most embodiments, although not necessarily, the compression causes a local enlargement of an outer cross-section at right angles to the compression axis. The term "outer cross-section" describes the cross sectional area encompassed by an outer contour of the element cut at right angles to the compression axis, i.e. the presence of possible cavities within the implant is disregarded in the calculation of the outer cross-section. In many cases—although not necessarily—an enlargement of the outer cross-section signifies an enlargement of the cross sectional area encompassed by a convex envelope (convex hull) of the implant body.

The coupling-in face is advantageously at least partly planar and extends at an angle to the compression axis. "At an angle to the compression axis" in this context means, "not parallel to the compression axis". The coupling-in face being perpendicular to the compression axis, i.e. at a right angle, is particularly advantageous. An angle between the compression axis and the coupling-in face of at least 45°, or better still, of at least 60° is generally preferred.

The thermoplastic material makes up at least a part of the implant; it may form the whole implant. Besides thermoplastics the thermoplastic material can also comprise non-thermoplastic components, such as reinforcing fibers, reinforcing splints, filling materials etc., or it may also constitute a partial or complete coating of an implant part of a non-liquefiable material (e.g. titanium) or a material which is liquefiable only at substantially higher temperatures (e.g. PEEK coated with PLA). Non-thermoplastic components can be evenly distributed in the thermoplastic material or be present in varying concentrations. The implant can further comprise areas free of thermoplastic material. Such areas may be of metal, glass, ceramic material, or of non-thermoplastic materials or thermoplastic materials liquefiable at substantially higher temperatures compared to the basic thermoplastic material.

The selected compression axis is generally a specific axis of the implant, i.e. the implant is fashioned such that compression along this compression axis is clearly defined and controlled and results in the desired local enlargement of the distance between the peripheral surface and the compression axis, i.e. the desired enlargement of the cross sectional area. In particular, the compression effect along the compression axis at a given (small) compressing force can be substantially greater than along other axes. Compression along other axes, such as perpendicular to the chosen compression axis, in addition or as an alternative will not result in an enlargement of the cross sectional area perpendicular to the chosen axis, cannot be carried out in a controlled manner and/or only with excessive energy unacceptable under conditions prevalent during surgical operations. In some embodiments, the compression axis may be marked by symmetry, e.g. the implant may be approximately rotationally symmetrical in relation to the compression axis.

The term "liquefied" describes a condition of the thermoplastic material in which it is plastic to the extent that, while under pressure, it can penetrate pores whose dimensions are smaller by at least one magnitude than a characteristic dimension of the implant. In this sense, "liquefied" also applies to thermoplastic material when it comprises a comparatively high viscosity of e.g. up to $10^4$ mPa·s.

The invention according to the first aspect treads a new path compared with the state-of-the-art technology. The state-of-the-art technology is familiar with methods of providing an opening (e.g. bore) in the osseous tissue and subsequently anchoring the—e.g. roughly pin shaped—implant in the opening by positioning it in the opening and applying ultrasonic vibration to it. During this process, the thermoplastic material of the implant may be liquefied on the circumferential surfaces of the implant and, if applicable, penetrate pores along the walls of the tissue opening. However, it is found that the anchoring effect of this 'non-pressurized' penetration into pores is often rather moderate. According to the state-of-the-art technology, it is possible to achieve a lateral pressure by shaping the tissue opening conically, which is elaborate. In contrast, according to the invention, pressure in lateral direction is increased by the compression and accompanying enlargement of the distance between compression axis and peripheral implant surface. This on the one hand increases the friction forces generated on the circumferential implant surface and causes the energy coupled into the implant via the mechanical vibrations to induce a liquefaction of the thermoplastic material precisely in that region, i.e. laterally, along the circumferential surface. On the other hand, the lateral pressure also drives the liquefied material into laterally existing pores or other structures (surface structures, cavities etc.) of the tissue opening and thus results in a particularly solid anchoring.

Hence the implant according to the invention makes it possible to exert pressure upon the lateral surfaces of the tissue opening. This enables an anchoring of the implant even in situations where no or very little pressure can be applied to the bottom of the tissue opening—e.g. because the bone is very brittle and/or very thin—or where the opening has no bottom because it is through-going. In such a case additional means for absorbing the compressing force must be provided. Such means are discussed in detail below.

The implant may be designed in various ways, wherein the compression of the implant is effected in corresponding various ways:

The implant consists of at least two separate components, wherein, due to their geometry, the components are shifted relative to each other under the effect of the compressing force. Shifting occurs along surfaces that are neither parallel with nor perpendicular to the compression axis but extend obliquely relative to the latter. The implant may be designed e.g. as a system of cones and/or wedges or as a system with a spreader element, which does not necessarily need to comprise thermoplastic material and e.g. is brought into the opening prior to the implant component(s) comprising thermoplastic material. The enlargement of the cross sectional area is effected either by the shifting of the implant components relative to each other (e.g. wedge system) or by shifting the implant components relative to each other and simultaneously spreading them (e.g. cone system).

The implant consists of at least two components linked via predetermined breaking points or predetermined liquefaction points, where the components are separated from each other when the compression force, and possibly also the mechanical vibrations, are applied. The required enlargement of the cross sectional area is effected by shifting of the implant components relative to each other as described for the previous example.

A separate element is provided in the opening for exerting a force counteracting the compressing force, wherein this element comprises a surface section which is oblique to the compression axis. The required local enlargement of the distance between the compression axis and the peripheral surface of the implant is effected by shifting the implant or a component thereof along the named surface, wherein the shifted component may or may not be spread.

The implant consists of one piece and comprises a section which is expandable by the compressing force. The implant is e.g. shaped like a hollow truncated cone, a hollow wedge, a hat or a tube and advantageously comprises slots to facilitate the expansion. The counterforce to the compressing force can be exerted on a surface perpendicular to the compression axis, or on a surface oblique to the compression axis. The latter case constitutes a combination with one of the three aforementioned embodiments.

The implant comprises at least one buckling location designed as a mechanically weak point (e.g. hole, slot, area of reduced wall thickness) or as a hinge. The local weak areas are softened during the implantation procedure, causing implant portions between the weak areas to tilt towards each other under the influence of the compressing force.

In other words: the compressing force causes either just shifting of the implant or of implant components (e.g. wedge systems), or shifting in combination with deformation (e.g. multi-part implants with spreadable components) or just deformation (e.g. one-piece implant able to buckle or to be expanded). Therein the shifting and/or the deformation can be supported by an appropriately shaped tool and/or by a separate auxiliary element. In the case of multi-part implants it is advantageous to design component surfaces, along which the components are shifted relative to each other, thus, that they are welded together during implantation. In the case of implants or implant components to be deformed, it is advantageous if the tensions caused by the deformation are resolved under the implantation conditions.

The implant or at least one of the implant components may comprise an elastically pliant, e.g. metallic (e.g. titanium) core; such a core may be formed of sheet material and comprise an edge which, during compression, is moved radially outwards and thereby cuts into the bone tissue, providing an additional anchoring.

"Oblique to the compression axis" means at an angle less than 90° and more than 0° relative to the compression axis. Advantageously, the oblique surfaces form an angle between 20° and 70° with the implant axis before implantation.

For physical reasons there is a counterforce to any acting force. If the opening in the bone tissue is a blind hole, the counterforce can be exerted by the bone tissue at the bottom of the opening. The invention according to its first aspect (as well as according to the second and according to the third aspect described below) however, is also especially suited to situations, where it is not possible or not desirable that the bone tissue absorbs the acting force (or, synonymously, exerts the counterforce). In many relevant advantageous, embodiments the force is imposed between a tool and a counter-element (retaining element). The counter-element may be placed and held in such a position that it does not transmit force to the bone tissue but that the force is exerted e.g. by the surgeon, by an assistant or by a suitable holder or device etc., whereas the implant is in contact with the hard tissue/hard tissue replacement material, and the liquefaction of the liquefiable material occurs in contact with the hard tissue/hard tissue replacement material.

A preferred embodiment of the implant consists entirely of the thermoplastic material. It may however also comprise a non-liquefiable core and still be compressible, e.g. if the core comprises several telescopic sheaths.

A second aspect of the invention provides a surgical device comprising an implant suitable for being anchored in bone tissue with the aid of mechanical vibrations as well as a tool (e.g. a sonotrode). The implant comprises a coupling-in face through which the mechanical vibrations are coupled into the implant and a material liquefiable by mechanical energy, which forms at least a part of the implant surface. The tool comprises a proximal side and a distal side, wherein the distal tool side comprises a coupling-out face suitable for coupling the vibrations out of the tool and adapted to the coupling-in face of the implant. A coupling between the tool and the implant is designed to withstand tensile force (force in a direction from the distal tool side towards the proximal tool side). The implant is anchored in the opening with the aid of mechanical vibration and a pulling force (causing a tensile load in the tool), whereby the thermoplastic material is at least partly liquefied, where in contact with the bone tissue, and pressed into the bone tissue in order to form a form-fit connection with the bone tissue when re-solidified. Alternatively, the device further comprises a counter-element (retaining element) suitable for exerting a counterforce (direction opposite to the force exerted by the tool) by which counterforce the counter-element is put under tensile force.

A corresponding method of anchoring an implant in bone tissue comprises the following steps:

providing an opening in the bone tissue;

positioning the implant on the bone tissue thus that thermoplastic areas of the implant are in contact with the bone tissue;

coupling a force and mechanical vibrations via the coupling-in face into the positioned implant, thereby liquefying at least part of the liquefiable material where it is in contact with walls of the opening and pressing it into the bone tissue in order to form a form-fit connection with the walls after re-solidification, wherein the force and the mechanical vibrations are coupled into the implant with the aid of a tool, wherein a proximal tool side is designed for mechanical vibrations to be coupled into the tool and the distal tool side comprises a coupling-out face through which the mechanical vibrations are coupled into the implant, and wherein the force coupled into the tool is a tensile force.

Whereas according to the state-of-the-art technology, a compression force is exerted on the tool for coupling a force into the implant. According to the second aspect of the invention, a tensile force is exerted on the tool for coupling a force into the implant. This very simple measure opens up a lot of new possibilities, some of which are outlined below:

Implantation in places difficult to access: the second aspect of the invention allows under certain circumstances implantations to be carried out from a non-accessible side.

Favoring a procedure which does not stress the bone tissue: by applying a pulling force to the implant and counteracting it with a simple counter-element—e.g. a simple perforated plate—practically all forces acting on the bone tissue can be eliminated (except the force necessary to ensure that the liquefaction of the liquefiable material can occur due to the contact between hard tissue/hard tissue replacement material and the implant surface).

Possibility of using newly developed implants and tools (sonotrodes).

For example, the coupling-out face of the tool faces "backwards", i.e. towards the proximal tool side. This is the case e.g. when the normal of the coupling-out face extends approximately parallel to the direction of the tensile force.

Alternatively, the implant is drawn through the opening in the bone tissue, i.e. a tensile force or pulling force is applied to the implant and moves the implant to a certain extent inside the opening.

Particularly advantageous is a combination of the first and the second aspect of the invention, i.e. the use of a compressible implant according to the first aspect in a device according to the second aspect, which device is designed such that in action a tensile force acts on the tool.

According to a third aspect of the invention, the implant is expanded by the tool, i.e. by causing the tool to move, in an axial direction, within the implant and thereby locally expands it in a lateral direction thereby causing the lateral walls of the implant to be pressed against walls of an opening in the bone tissue or other hard tissue or hard tissue replacement material.

A method according to the third aspect, the method for anchoring an implant in bone tissue, where the implant comprises an axis as well as a material liquefiable by mechanical vibrations, which forms at least a part of the surface of the implant, accordingly, features the steps of providing an opening in the bone tissue;

positioning the implant in the opening;

providing a tool having a proximal portion and a distal end portion;

positioning the tool in contact with the implant;

coupling the mechanical vibrations into the tool and simultaneously moving the implant relative to the implant in an axial direction, a portion of the tool moving in an interior of the implant, and thereby expanding the implant and pressing the implant at least locally against lateral walls of the opening and, due to the expansion and the effect of mechanical vibrations coupled into the implant from the tool, liquefying the thermoplastic material at least partly where in contact with the wall of the opening to yield liquefied thermoplastic material, and pressing the liquefied material into the bone tissue in order to form a positive-fit connection with the wall after re-solidification.

The implant may comprise an axial implant opening, through which the tool (or a distal end thereof) is preferably moved.

A surgical device according to the third aspect of the invention comprises an implant suitable for being anchored in bone tissue with the aid of mechanical vibrations and a tool, which implant comprises an axis and an axially extending implant opening as well as a material liquefiable by mechanical vibrations, which forms at least a part of the surface of the implant, and which tool has a proximal portion and a distal end portion, wherein the distal end portion has at least one cross-section which is larger than at least one cross-section of said recess in the implant and which distal end portion is able to be moved within the implant opening relative to the implant under the influence of a force and of the mechanical vibrations, whereby the implant is locally expanded under at least partial plastification of the implant, wherein the mechanical vibrations are able to be transmitted to a peripheral surface of the implant in the area of the expansion.

This means that embodiments of the third aspect of the invention are based on the fact that, with the aid of the tool, the thermoplastic material is liquefied or plastified in a peripheral implant region and advantageously also in the area of the axially extending recess and is pressed radially outward. As with the procedure according to the first aspect, with this procedure too an anchoring is achieved by means of interpenetration of bone tissue structures in a lateral wall of the opening in the bone tissue. Many relevant advantages and freedom of design of the first aspect of the invention also apply to the third aspect of the invention.

According to a preferred embodiment of the third aspect of the invention, the implant consists entirely of the thermoplastic material or of a plurality of thermoplastic materials.

Particularly advantageous is a combination of the second aspect of the invention and the third aspect, i.e. a procedure according to the teaching of the third aspect, wherein the force is coupled into the tool as a tensile force.

According to a further embodiment of the third aspect of the invention, the implant is expanded by the tool and therefore pressed against the lateral walls of the opening, is not anchored in these lateral walls by means of a liquefied material but by other means, e.g. by surface structures acting like barbs.

Objects of the invention are also sets of items for carrying out the method according to one of the three aspects of the invention. Such a set comprises at least one tool (e.g. sonotrode) as well as one or advantageously a plurality of implants. In addition, the set may comprise a device for the generating the mechanical vibrations, instructions for the implantation, a counter-element (retaining element), a separate element with an oblique surface area as discussed above and/or further items.

In embodiments of any one of the three aspects of the invention, the tool may, after implantation, be removed, or it may remain in place and, for example, affixed to the implant by re-solidified material that was at least partly liquefied during implantation. In the latter cases, the tool may, after implantation, serve as a functional part of the implant. It may for example be used in a load bearing manner, e.g. being a pin or a the load bearing part of a joint prosthesis, (stem), and may comprise means for affixing a further element to it such as a structure for forming a positive fit connection (such as a threading, a bayonet fixing, an eyelet for a thread or suture etc., or a structure which an other element may be glued etc.

In embodiments that feature automatically applying the acting force, as well as in other embodiments where the force is applied manually, there may optionally be a stop defining the travel of the tool during implantation.

The methods and implants described herein may be used for connecting two parts of the human or animal skeleton, or for connecting one part of the skeleton and a soft tissue part, or for connecting at least one part of the skeleton and another object. The implants described herein may also be endo-prostheses such as e.g. joint prostheses, bone prostheses, intervertebral disc prostheses, artificial ligaments or tendons, artificial teeth, etc. According uses of implants as such are known in the art, and the methods and implants according to the invention may differ from known methods and implants primarily in their structure and in the here-described way the connection to the hard tissue is achieved. Alternatively, the methods and implants may also be used for new applications in surgery, some of them being only made possible by the invention according to any one of the above-described aspects.

Some of the new applications of implants are described in this text. These applications described herein are mere examples of new uses the approach according to the invention makes possible, the new applications being by no means restricted to the described examples.

A category of applications concerns the re-surfacing of joint parts. Examples of re-surfacing techniques have for example been described in U.S. provisional patent application No. 60/913,012, that is incorporated herein by reference. According to re-surfacing applications, an element is fixed to remaining bone material by an implant according to any aspect or combination of aspects of the invention. The element may comprise a coating replacing the cartilage of the joint part, or such a coating may be applied to the element after its fixation.

Another category of applications is the fastening of support elements (such as screws or plates) fixing the relative position of bone fragments after a fracture or after insertion of bone replacement fragments or bone replacement material. Such a support element may, according to the present invention, be fixed, in one or more locations, by an implant according to any aspect or combination of aspects of the invention.

An even further category of applications is the replacement of conventional surgical screws by implants according to any one of the aspects of the invention or according to any combination of aspects.

Yet another category of applications concerns the anchoring of a suture by means of an implant according to any aspect or combination of aspects of the invention. The suture may be fixed to the implant (or an element fixed by the implant) prior to implantation, by implantation, or it may be fixable to such element after implantation.

In the following, embodiments of the invention are described in connection with the following Figures, wherein the same reference numerals are used for same or equivalent elements. Therein:

BRIEF DESCRIPTION OF THE DRAWINGS

FIGS. 1a and 1b illustrate a first embodiment of the invention according to its first aspect;

FIGS. 2a and 2b show a sectional view of the embodiment according to FIGS. 1a and 1b in an opening in the bone tissue to illustrate its function;

FIGS. 3a to 3c are sectional views (not showing the contact with the bone tissue) of further embodiments of the invention according to its first aspect;

FIGS. 8a and 8b show a further embodiment of the invention according to its first aspect;

FIG. 9 shows a further embodiment of the invention according to its first aspect;

FIG. 10 shows an embodiment of the invention according to its first aspect, wherein the implant comprises a non-liquefiable core;

FIG. 11 shows a further embodiment of the invention according to its first and second aspect;

FIGS. 25a and 25b illustrate the principle of the fixation of a screw replacement implant; and FIG. 26 illustrates a possibility of resurfacing a joint using an implant according to the invention.

DETAILED DESCRIPTION OF THE INVENTION

Figure 3C:
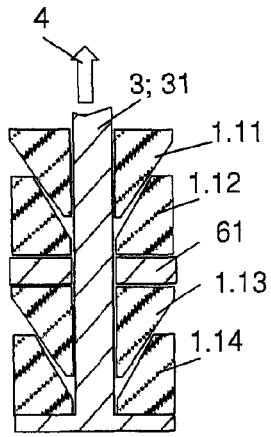

The implant 1 according to FIG. 1a is a first example of an implant according to the first aspect of the invention. The implant is essentially tubular, consists of a thermoplastic material, and comprises a proximal end face 1.1 and a distal end face 1.2. The implant further comprises at least one slot 12 extending approximately parallel to the axis 11 of the implant; advantageously there are two, three or more than three slots arranged approximately equidistantly. Due to the slot or slots 12 the implant is compressible by a compressing force 4 acting parallel to its axis (according to FIG. 1a, the axis 11 of the tubular implant is also its compression axis). The implant is depicted in a compressed state in FIG. 1b.

It is obvious that for achieving the desired compression, a force must act upon the implant from two opposite sides ("force and counterforce"), wherein the counterforce is often exerted by a stop face. In the embodiment according to FIGS. 1a and 1b compressing forces are exerted upon the proximal end face 1.1 and the distal end face 1.2. In the following description however, a force is illustrated only where a tool is in action. To the expert it is obvious that a counterforce must exist in order to achieve the desired effect.

According to the invention the implant is designed thus its compression results in a local enlargement of the distance between the peripheral implant surface and the compression axis 11, here, a local enlargement of the exterior cross-section perpendicular to the compression axis 11. The enlargement can occur anywhere between the proximal end face 1.1 and the distal end face 1.2. In the example according to FIGS. 1a and 1b the enlargement is, due to the symmetry of the implant, greatest in the middle between the end faces. In FIGS. 1a and 1b, the diameter of the outer cross section—this also incorporates the cavity within the implant—is indicated at the point of the largest cross section by c in the non-compressed condition, by c' in the compressed condition. Through the compression, the slots 12 become wider.

For implantation, the implant 1 is placed in an opening 21.1 in bone tissue 21. As illustrated in FIG. 2a this opening can be a blind bore. Alternatively the opening is tunnel-shaped, i.e. reaches through the bone (for more detail see further below). In particular, the opening can be of a cylindrical shape, which is easy to be made. The diameter of the bore is at least equal to the diameter c of the outer cross section of the original outer cross section and may be slightly larger, as shown in FIG. 2a.

When the implant is positioned in the opening 21.1, a force 4 is exerted along its compression axis 11 and mechanical vibrations 5 are coupled into the implant while the force 4 is active. This is achieved with the aid of a tool 3 comprising a coupling-out face 3.1, which collaborates with a coupling-in face of the implant. In the illustrated example the coupling-in face corresponds with and is identical with the proximal end face 1.1. The coupling-out face 3.1 can completely cover the proximal end face 1.1 and the interior cavity of the implant 1, as shown, but it can also be ring-shaped and exactly adapted to the proximal end face 1.1. The tool 3 is effectively connected on its proximal side 3.2 with a vibratory device (not shown). Such devices are generally known and have been referred to e.g. in WO02/069817.

FIG. 2b shows the implant 1 after application of the compressing force and the vibrations. Due to the compressing force 4 the cross-section of the implant is enlarged, as illustrated in FIG. 1b. As soon as the implant engages in areas of the cross-section enlargement with the lateral wall of the opening, the compressing force 4 produces a pressure upon the lateral walls. There the vibrations cause friction and the thermoplastic material is locally liquefied and pressed into pores or other cavities in the bone. This effect is indicated by horizontal arrows in FIG. 2*b*. Of course the same also occurs in the area of the distal end face of the implant.

Once a predetermined compression is achieved, the vibrations are switched off and/or the tool 3 is removed. The liquefied thermoplastic material re-solidifies and creates an anchoring of the implant 1 through a form-fit connection with the structures of the lateral wall.

The method of anchoring the implant with the aid of thermoplastic material which is liquefied and in the liquefied state penetrates into cavities (pores, other cavities of small dimensions when compared with the opening provided in the bone tissue for the implant), which method is illustrated in FIG. 2*b*, is shared by all the embodiments of the invention. In each following Fig. this effect is illustrated by arrows indicating the direction in which the thermoplastic material penetrates into the cavities.

Preferably but not necessarily, as in all embodiments according to the first aspect of the invention, the thermoplastic material of the implant is heated during the implantation procedure to such an extent that it is free of tension after the implantation procedure, i.e. no force counteracting the implant deformation remains. In this case the compressing force and the mechanical vibrations can be stopped simultaneously as the implant does not relax, neither before nor after re-solidification.

The implant 1 according to FIG. 3*a* comprises a plurality of components. The illustrated example consists of three components 1.11, 1.12, 1.13, which are approximately rotationally symmetrical with regard to any rotation angle around its axis, which also corresponds with the compression axis 11. The first component 1.11 (seen from the distal side) has essentially the shape of a truncated cone and comprises an axial bore through it. The second component 1.12 has essentially the shape of a hat, here with a central axial bore. The hat-like design defines an interior surface 1.12*a* and an exterior surface 1.12*b*. The third component 1.13 has the shape of a cylinder and comprises a coaxial conical cavity and an axial bore. The central bores of the first, second and third component are coaxial to each other and of approximately the same diameter.

If applicable and deviating from the rotational symmetry, at least the central component 1.12, but possibly also the third component 1.13 and the first component 1.11, are advantageously slotted, which is not shown in FIG. 3*a*. Because of the slot(s) the relevant components are easily spreadable and the implant as a whole can be compressed along the compression axis by a relatively moderate compressing force. As the compressing force 4 is applied the components 1.11, 1.12, 1.13 are shifted relative to each other along surfaces extending obliquely (i.e. at an angle or neither parallel nor perpendicular) to the compressing force. In the illustrated embodiment, the named surfaces have the form of truncated cone shells, i.e. they are conical. There are other surfaces also which have a spreading effect.

In the illustrated embodiment, the opening angle of the exterior surface 1.11*a* of the first component 1.11 is larger than the opening angle of the interior surface 1.12*a* of the second component 1.12 and the opening angle of the exterior surface 1.12*b* of the second component 1.12 is larger than the opening angle of the interior surface 1.13*a* of the third component. Advantageous for the spreading effect in the present configuration is that at least one opening angle of an exterior surface is greater than the opening angle of an interior surface, into which the exterior surface reaches.

When the implant is positioned in the opening in the osseous tissue—diameter of opening approximately corresponding with the outer diameter of the implant components 1.11, 1.12, 1.13 before compression—and when compressing force and mechanical vibrations are applied, the following takes place:

Due to the compressing force, the second and the third component 1.12, 1.13 are spread, resulting in an enlargement of the outer cross sectional area of the second and third component and thus of the whole implant.

Due to the spreading outer surfaces, the second and third component 1.12, 1.13 are pressed against the lateral wall of the opening. Due to the mechanical vibrations the thermoplastic material liquefies in these surface areas and interpenetrates the pores (or other cavities) in the osseous material 21.

The vibrations also result in frictional forces between the surfaces 1.11*a*, 1.12*a*, 1.12*b*, 1.13*a* which cause the thermoplastic material to liquefy, which in turn results in the first, second and third components being welded together.

The proximal end face 1.1 or alternatively, the distal end face 1.2 of the implant according to FIG. 3*a* can serve as a coupling-in face. The proximal and the distal side of the implant can be exchanged (i.e. the implant can be used "back to front").

FIG. 3*b* shows a further embodiment of the implant according to the invention, which implant is, regarding compression and implantation, very similar to the embodiment according to FIG. 3*a*. Same elements are designated with same reference numerals. The implant is a multi-part implant and consists of any chosen number (e.g. three as shown) of identical components, all designed for being spread (e.g. hollow cones or hollow wedges) and loosely positioned inside one another. The compressing force 4 pushes the spreadable components together and spreads them. If need be, the distal end portion of a tool to be used is designed as a spreading element, as illustrated in FIG. 11. In the embodiment according to FIG. 3*b* all surfaces oblique to the compression axis, along which the implant components are shifted in relation to each other, may be parallel (identical opening angles), as illustrated in FIG. 11. This has the advantage that a user—e.g. a surgeon—can determine the size of the implant by choosing the number of identical components.

The embodiment according to FIG. 3*c* is based on the embodiment according to FIG. 3*a*. Unlike that embodiment however, the implant consists of a plurality of modules (illustrated: two modules) each of which comprises at least one component 1.11, 1.12, 1.13, 1.14 (illustrated: two components per module). There is a spacer element 61 between the modules, e.g. illustrated as a metallic ring, which does not need to be of thermoplastic material. This embodiment is suitable for being anchored at two or more locations in a lateral wall of the opening in the bone tissue. The distance between these locations is determined by the spacer element. Such implant embodiments comprising two modules are advantageously used in combination with a tool 3 or counter-element 31, whose function is discussed in more detail below. As shown in FIG. 3*c*, the tool or counter-element 3, 31 comprises a shaft penetrating a central recess of the implant. Other guiding means for guiding the spacer element are conceivable.

In addition to the embodiments illustrated in FIGS. 3*a*, 3*b* and 3*c*, the following embodiments (besides many others) are conceivable:

Each component may comprise a non-liquefiable core, the core of the second and third component being elastically or plastically deformable. The core, which e.g. consists of titanium, may constitute a substantial part of the cross-section and form the load-bearing part of the implant.

The first component 1.11 does not necessarily need to comprise thermoplastic material.

The first component may be removable after implantation (in which case it is not part of the implant but e.g. part of the tool or a separate element).

An equivalent embodiment comprises instead of three components only two components (e.g. no central component 1.12) or four or more than four components (e.g. further hat-shaped components similar to the central component 1.12).

The shapes of the components may be varied, wherein it is necessary to provide some surfaces oblique to the compression axis, along which surfaces the components are able to be shifted relative to each other.

The components do not need to be approximately rotationally symmetrical. The central bore may be omitted.

The components may be linked prior to the implantation via predetermined breaking points, which will be discussed in more detail below.

The components do not need to be hat-shaped and able to be spread but may be laterally displaceable relative to each other, which is also described in more detail below.

For a selective liquefaction of thermoplastic material in a desired location, at least one energy director may be provided along the periphery of at least one component.

The embodiments according to FIGS. 3*a* to 3*c*, the same as the embodiments according to the first aspect of the invention as described below, may comprise an elastically ductile core of a material, which, under implantation conditions, is non-liquefiable. At least the implants with components which have the shape of hats or hollow wedges can e.g. be made of sheet metal which is slotted and coated with thermoplastic material, wherein the metal sheet may protrude radially from the implant component. During compression, the metal sheet is spread and cuts e.g. into the bone tissue of the lateral wall of the opening. The implant may be additionally furnished with elements acting like barbs. The cutting effect of the metal sheet provides an additional anchoring.

Any chosen combinations of the named embodiments are possible.

Figure 4:
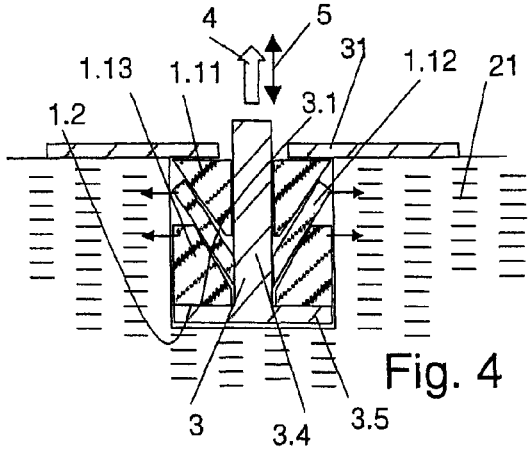
FIG. 4 is a sectional view of the embodiment according to FIG. 3a in a configuration which also corresponds with the second aspect of the invention.

In FIG. 4 the implant 1 according to FIG. 3 is shown in a configuration corresponding with the second aspect of the invention. In this configuration, no force is exerted on the bone tissue on the bottom of the opening. The vibrations and the compressing force acting upon the implant are coupled into the implant from a tool 3 which is under tensile force. The configuration according to FIG. 4 is therefore also suitable for applications in tissue openings leading tunnel-like through the bone tissue.

The tool 3—as it serves among other things to couple vibrations from a vibratory device (not illustrated) into the implant, it can also be called a 'sonotrode'—comprises a shaft 3.4 and a base plate 3.5. The shaft and/or the base plate can make up a substantial part of the cross-section of the device consisting of tool and implant and can be left in the implant to form the load-bearing implant part. For such purposes, the shaft and/or base plate are made, e.g. of titanium. The coupling-out face 3.1 of the tool is the surface of the base plate 3.5 facing towards the proximal tool side. The shaft 3.4 extends through the central bore of the implant-components 1.11, 1.12, 1.13 and protrudes from the proximal end of the implant and from the opening in the bone tissue. The proximal tool end is designed for being coupled to a vibratory device, which coupling is to be suitable for transmitting a tensile force.

During the implantation procedure, a tensile force is applied to the tool 3 (force 4) and mechanical vibrations 5 are coupled into it. From the tool, force 4—as compressing force—and the mechanical vibrations are coupled into the implant. A counter-element 31 prevents the implant from simply moving out of the opening in the bone tissue. In the illustrated example the counter-element 31 is designed as a plate.

Following the implantation procedure, the tool 3 can be dealt with in various ways:

The tool can remain in the place of the implantation. This embodiment is particularly advantageous when the tool is designed for a further function. Thus the tool can serve e.g. for attaching a further element on the implant, e.g. a suture, a ligament, a tendon, another bone, an endoprosthesis or any other element. The tool can be designed for practically any function known to be functions of implanted objects.

If the opening in the bone tissue is a through-going opening, the tool can be separated from the vibratory device and be removed from the distal side of the implant.

The tool can be removed from the proximal side. In this case the tool and the through-going recess in the implant, through which the shaft 3.4 extends during the implantation procedure, must not be of a round cross section (no rotational symmetrical with regard to random rotation angles). Corresponding implant openings will be discussed in more detail below.

Like the implants according to FIGS. 1 and 3, the implants according to the FIGS. 5 to 10 are designed according to the first aspect of the invention and can be used together with a suitable tool in a configuration according to the second aspect of the invention.

Figure 5:
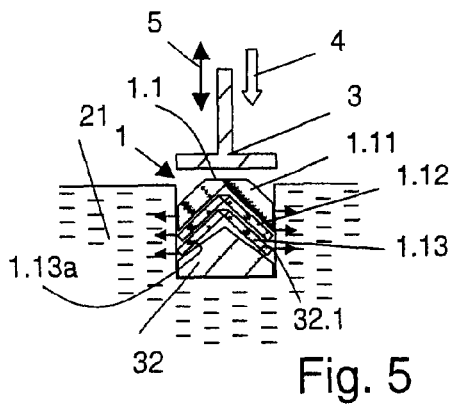
FIG. 5 is a sectional view of a further embodiment of an implant in an opening in the bone tissue.

The implant 1 according to FIG. 5 comprises, like the one according to FIG. 3, a plurality of components 1.11, 1.12, 1.13, which are designed for being shifted relative to each other along surfaces that extend obliquely (i.e. at an angle or neither parallel nor perpendicular) to the compressing force. The components can be designed just like the implant components—in particular the second and/or third component—of the embodiment according to FIG. 3 and its variants and are therefore not described in detail again. In contrast to the embodiment according to FIG. 3, a separate spreading element 32 is used, wherein the spreading element does not need to comprise thermoplastic material. As illustrated, the spreading element is placed on the bottom of the opening in the bone tissue 21 before the implant is introduced. The spreading element comprises at least one shifting surface 32.1, which is oblique relative to the compression axis and forms an angle with the latter which is greater than the opening angle of the corresponding interior surface 1.13*a* of the implant. The components 1.11, 1.12, 1.13 are spread by the compressing force 4 due to the effect of the spreading element and in the area of their circumference are pressed against the lateral wall of the opening in the bone tissue. During the implantation procedure, the spreading element can be welded to the components 1.11, 1.12, 1.13 comprising thermoplastic material such becoming part of the implant. Depending on the surface properties, the spreading element may also remain separate. In the illustrated configuration the spreading element remains in the opening in the bone tissue where it may or may not have a medical function. In other configurations it may be removable from the opening.

The spreading element—whether or not it comprises material liquefiable during implantation—may optionally be configured to be connected to the implant 1—and to become part of it—during implantation, for example by welding and/or by other means of forming a connection.

The following embodiments are conceivable in addition to the previously described embodiments:

Instead of three components there may be a single component, two components or four or more components, comprising thermoplastic material at least in a peripheral region.

The implant may also be placed the other way round, provided that the expansion element is correspondingly adapted.

Combinations with the variants as described in connection with the embodiment of FIG. 3 are possible.

The spreading element may be omitted, in which case the implant components are placed upon a surface approximately perpendicular to the compression axis—e.g. the bottom of the opening—which surface exerts the counterforce. This embodiment is equivalent to the one shown in FIG. 3*b*.

Figure 5A:
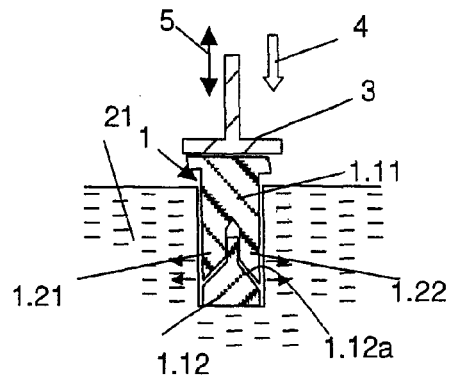
FIG. 5a is a sectional view of an even further embodiment of an implant in an opening in the bone tissue.

FIG. 5*a* shows a variant of the embodiment of FIG. 5. It differs in that the spreading element 1.12—being a second part of the implant—is made of thermoplastics and is welded together with the first implant part 1.11 during the implantation process. The first implant part 1.11 comprises two legs 1.21, 1.22 that are spread apart by the spreading element 1.12.

The depicted first implant part 1.11 further comprises, at its proximal end, a thermoplastic implant head with a larger cross section than a main portion of the implant.

Of course, also combinations of the approaches of FIGS. 5 and 5*a* are possible, for example a first implant part with two legs 1.21, 1.22 to be spread apart may be combined with a spreading element of not thermoplastic material, or a spreading element 1.12 of thermoplastic material may be combined with a first implant part with a slitted hat-like distal end portion etc.

Figure 6:
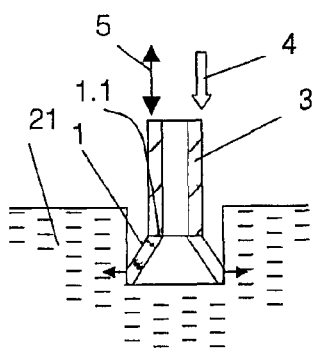
FIG. 6 is a sectional view of a further embodiment of an embodiment of the invention according to its first aspect.

FIG. 6 shows yet another variant of the embodiment according to FIG. 5. This differs from the latter by not comprising a separate (spreading) element with a surface section oblique to the compression axis. Instead, spreading is achieved by the shape of the implant 1 and by the implant being pushed against an e.g. level surface perpendicular to the compression axis, which may be the bottom of the opening in the bone tissue as illustrated, or the surface of a separate element. In the illustrated example, the implant is hat-shaped and the compressing force 4 squeezes the edges outwards, thus, pressing them against the lateral walls of the opening. Advantageously the hat-shaped implant comprises a slot or a plurality of slots as described further above. Variants with other spreadable shapes (e.g. hollow wedge) are also conceivable.

FIG. 6 moreover illustrates, that the tool 3 can be of a specific shape adapted to the coupling-in face 1.1—here at least on the distal side tubular. Such a specific shape enables an energy-efficient coupling of mechanical vibrations into the implant.

Figure 7:
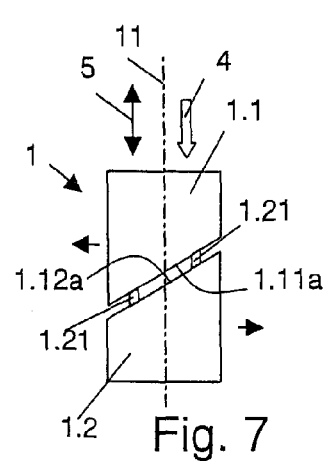
FIG. 7 illustrates the functional characteristics of a further group of embodiments.

The embodiment of the implant 1 according to FIG. 7 comprises two components. A first proximal component 1.11 is connected to the second distal component 1.12 by connecting fins 1.21, which are thin compared to the dimensions of the implant. During compression of the implant the fins 1.21 break or melt, i.e. they represent predetermined breaking or melting points. The first component 1.11 and the second component 1.12 are wedge-shaped, each comprising a ramp 1.11*a* and 1.12*a* which slide sideways along each other when the components are pressed against each other by a compressing force acting along the compression axis 11.

After disintegration of the connecting fins 1.21, the implant components 1.11, 1.12 are shifted relative to each other under the influence of the compressing force. The embodiment according to FIG. 7 is therefore a further example of an implant comprising a plurality of components 1.11, 1.12, movable relative to each other along surfaces (i.e. ramps) extending obliquely to the compression force. In this embodiment too, an outer diameter of the implant is enlarged by the lateral shift caused by the compressing force.

Connections like the connecting fins 1.21 serving as predetermined breaking or melting points can, as already mentioned, also be applied in the multi-part embodiments discussed further above.

The design of the shifting surfaces oblique to the compression axis 11 as ramps—with or without connections between the components—may also be combined with the characteristics of the embodiments of FIGS. 3 and 5.

In particular one of the implant components may be replaced by a separate element which does not need to comprise thermoplastic material and functions in an analogous manner as the spreading element according to FIG. 5.

Alternatively to the illustrated embodiment, an implant according to FIG. 7 can also be designed to be thermoplastic and essentially cylindrical (e.g. circular cylinder) with horizontal (i.e. perpendicular to the cylinder axis) or oblique incisions, which do not reach right through the implant but leave areas of a reduced cross section. These serve as predetermined breaking or melting points. Such an embodiment may be advantageous with regard to production.

FIG. 8*a* shows a further embodiment of an implant 1 according to the invention. In this embodiment, as opposed to the previously described embodiments, the local enlargement of the distance between a peripheral surface and the compression axis is not necessarily due to an enlargement of the exterior cross sectional area. In this and other similar examples however, at least the projection of the exterior surface along the compression axis is enlarged.

The implant is essentially pin-shaped, but comprises lateral incisions 14, 15 and corresponding contractions 1.4, 1.5. During implantation these contractions function as predetermined melting points. As they melt, or at least soften, due to the effect of the mechanical vibrations, the compressing force tilts the implant sections between the contractions towards each other such effecting the local enlargement of the distance between the peripheral implant surface and the compression axis, as shown in FIG. 8*b*, which illustrates schematically the shape of the implant after implantation. The regions being pressed against the lateral walls of the opening in the bone tissue are indicated by horizontal arrows. The effect of liquefaction (the liquefied material being pressed into structures of the bone material) then takes place where the implant is pressed against the lateral wall.

Alternatively, the implant may comprise just one contraction 14, or two contractions (or possibly more than two contractions) with differing cross-sections. In particular the implant may comprise a wider contraction closer to the coupling-in face. This can result in the contraction further removed from the coupling-in face liquefying before the contraction closer to the coupling-in face and may prevent the contraction closer to the coupling-in face from melting before the other contraction, which would inhibit further transmission of mechanical vibrations to this other contraction.

FIG. 9 shows an embodiment of an implant 1 according to the invention designed in the manner of an accordion, wherein portions 1.31 linked by hinges 1.32 are moved into a steeper position in relation to the compression axis 11 under the influence of the compressing force 4. Thereby the outer cross-section of the implant is enlarged locally. In the illustrated embodiment the whole implant 1 is a single unit, so that the hinges 1.32 are created simply by the shape of the implant body; the use of other hinging means is possible. In certain circumstances, measures can be taken to enable mechanical vibrations to be transmitted to the areas further removed from the coupling-in face. Such measures are e.g. the provision of a non-liquefiable core of superior rigidity compared to the thermoplastic material.

Such a core is shown in FIG. 10 in an embodiment similar to the one of FIG. 3. Elements equivalent to the corresponding elements of the embodiment according to FIG. 3 are not again described in detail. The core comprises two core components 41, 42, which are moveable against each other. The first core component 42 comprises, in the illustrated embodiment, a base plate 42.2 and an adjoining sheath-like section 42.1. The exterior or interior surface of the base plate 42.2 can serve as a coupling-in face for the mechanical vibrations. The second core component 41 is here designed as a sheath moveable inside the sheath-like section 42.1 of the first core component. While the implant is compressed one core component slides inside the other.

Alternatively to the two-part core, one-piece cores or multi-part cores are also possible. A one-piece core does not extend across the entire length (relating to the compression axis 11) of the implant, because that would render a compression of the implant impossible.

FIG. 11 shows a configuration with a compressible implant 1 according to the invention of the kind described in connection with FIG. 5. In contrast to the latter, there is no separate spreading element but the tool 3 comprises a wedge- or ramp-like coupling-out face 3.1 that is formed by a distal end portion 3.7 being larger in diameter than a shaft portion 3.4. The wedge- or ramp-like coupling-out face 3.1 serves to couple mechanical vibrations and the compressing force into the implant as well as to spread the implant.

In the configuration illustrated in FIG. 11, moreover, the principle of the tool 3 under tensile force is applied. The configuration according to FIG. 11 is therefore also suitable for use in tissue openings with a bottom which is not suitable to be loaded or in a through-going opening (tunnel) as illustrated in FIG. 11.

The principle of coupling a force into the implant which puts the tool under tensile loading corresponds with the second aspect of the invention. This principle can also be applied in connection with implants which are not compressed by the named force. Such configurations are described in connection with the following FIGS. 12 to 16.

Figure 12A:
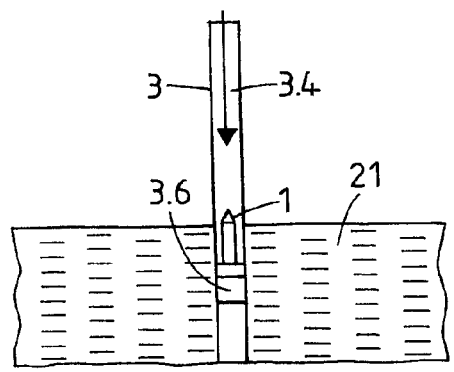
FIGS. 12a to 12d illustrate the principle of a device and a method according to the second aspect of the invention.
Figure 12B:
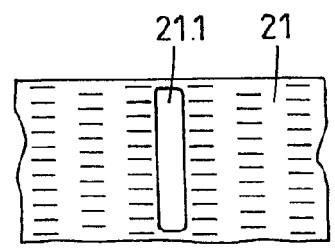

FIGS. 12a and 12b show, in section and viewed from the top, a bone tissue 21 comprising a slot-shaped (not round) opening 21.1 reaching tunnel-like from one surface to the opposite one. FIG. 12a also shows a tool 3 with a shaft 3.4 and a reach-out portion. In the illustrated embodiment the reach-out portion is a traverse 3.6 oriented perpendicular to the shaft. Two implants of thermoplastic material—possibly with a solid non-thermoplastic core—are fixed to the traverse 3.6 in a reversible manner.

Figure 12C:
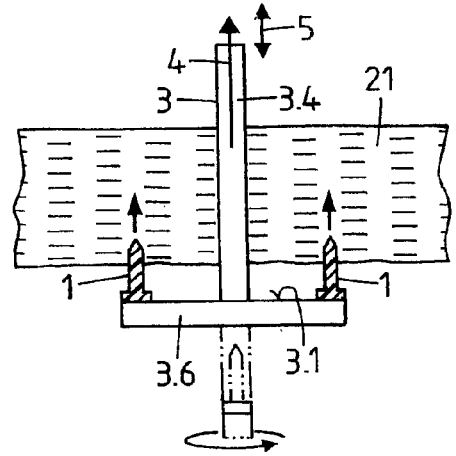

As illustrated in FIG. 12a, the tool 3 with the implants attached thereto is moved in a first step from a proximal side of the bone through the opening until the implants 1 are completely outside the bone tissue. Subsequently, as shown in FIG. 12c, the tool is rotated around an axis defined by its shaft 3.4, e.g. by 90°. Then, as in the previously described embodiments, a force is coupled into the implants pressing the thermoplastic material of the implants against the bone tissue. This is achieved by pulling the tool backwards, thereby pressing the implants against the rear side of the bone tissue. While the force is acting upon the implants, mechanical vibrations are coupled into the implant via the coupling-out face 3.1 of the tool, which is here the proximal surfaces of the traverse upon which the implants are fixed. This causes the thermoplastic material of the implants to partly liquefy and to be pressed into the bone tissue. After stopping the mechanical vibrations, the thermoplastic material re-solidifies and forms a form-fit connection with the bone tissue.

Figure 12D:
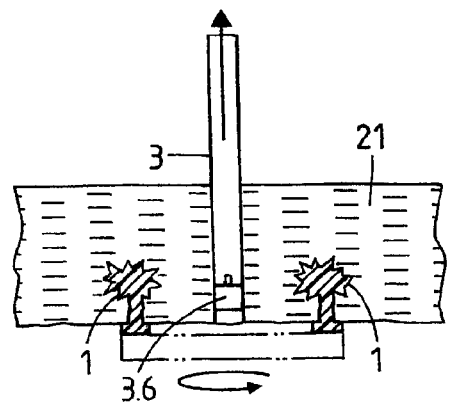

As shown in FIG. 12d the tool is subsequently removed by being detached from the implants now anchored in the bone tissue by a gentle push. Then it is turned back into the orientation in which the reach-out section fits through the opening 21.1 and is retracted. Alternatively to the illustrated embodiment, it is also possible that the tool is left in the bone tissue after implantation and there e.g. assumes another function. It is also possible to remove just a part of the tool, e.g. the shaft, while another part, e.g. the reach-out portion, remains and assumes a further function. In such a case the tool is not a single unit but shaft and reach-out portion are attached to each other in a reversible manner, e.g. by being screwed together.

The embodiment of the invention shown in FIGS. 12a to 12d is also suitable for securing two pieces of bone, which, prior to the implantation, are separated from each other or connected only by a weak link, together from "behind", i.e. from a side not easily accessible. In such a case the tool is not introduced through an opening as illustrated in FIG. 1b but through the gap between the two bone sections. The reach-out portion of the tool remains in place after the implantation and serves as a bridge connecting the two bone sections in a rigid manner.

In the illustrated embodiment, no openings are provided in the bone tissue for positioning the implants prior to the application of the mechanical vibrations. The opening 21.1 in the bone tissue merely serves for positioning the tool. The implants are driven into the bone tissue by a force exerted upon them, wherein an implant tip and/or axially extending cutting edges, advantageously not consisting of the liquefiable material, support penetration of the implant into the bone tissue.

The force for driving the implants into the bone tissue can e.g. be applied before the mechanical vibrations. Alternatively to the illustrated configuration, it is also possible to provide openings in the bone tissue, wherein the diameter of these openings may be smaller than the diameter of the implants.

The following variants are possible:

Instead of with two implants as illustrated, the method can also be performed with just a single implant or with more than two implants.

The reach-out portion of the tool can have any shape optimized for its function as well as for the transmission of vibrations and force.

Depending on circumstances the tool with the implants can be introduced from behind (i.e. from the distal side) so that only the shaft has to be moved through the opening in the bone.

Figure 13:
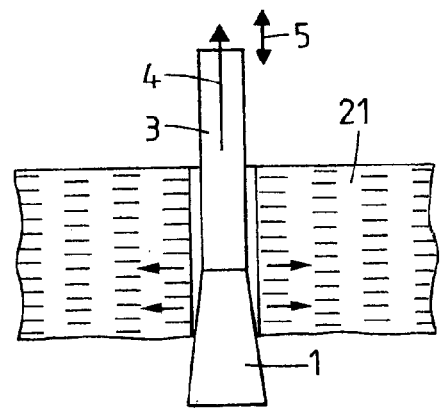
FIGS. 13, 14a, 14b show further embodiments according to the second aspect of the invention.

FIG. 13 shows a further embodiment of the invention. A through-going opening having a constant cross section (e.g. a through-bore with a round cross section) is provided in the bone tissue 21. An implant 1 tapering from the distal side to the proximal side is introduced from behind, i.e. from the distal side into the opening. The implant is drawn into the opening with the aid of the tool 3, which engages the proximal side of the implant, wherein a tensile force acts on the tool (the tool is under tensile loading). While the tensile force is kept active the mechanical vibrations are coupled into the implant. The vibrations and the slightly tapering shape of the implant cause the thermoplastic material in the area of the circumferential surface of the implant to be liquefied and to be pressed into pores or other cavities on the lateral walls of the opening in the bone tissue.

In this embodiment, where tensile forces not only impinge on the tool but also on the implant, it is necessary to connect the tool and the implant rigidly, as described in more detail below.

As a—often less preferred—variant, the opening may taper toward the proximal side while the implant is cylindrical.

As a further variant, the opening in the bone tissue can be stepped, wherein it is wider on the distal side than on the proximal side. The corresponding implant may comprise a shoulder engaging the step of the opening during the implantation procedure. Further embodiments of implants, which can be implanted by means of pulling force, are conceivable.

Figure 14A:
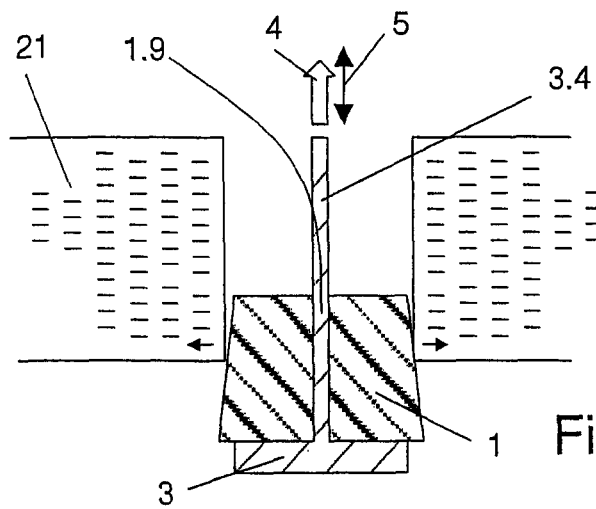

FIG. 14*a* shows a configuration with a slightly conical implant 1 being moved, like the implant according to FIG. 13, with the aid of a tool 3 along an axis of the opening in the bone tissue, wherein the force to be coupled into the implant puts the tool under tensile force, i.e. the force acting on the implant is directed against the oscillation generator. However, in contrast to the configuration according to FIG. 13 the force upon the implant 1 is a pushing force and pushes the implant into the opening. To this end the implant comprises a central bore (recess) 1.9, which in the illustrated configuration extends parallel to the axis of the opening in the bone tissue during the implantation procedure. A tool shaft 3.4 carrying a base plate 3.5 extends through the bore 1.9. The force to be coupled into the implant as well as the mechanical vibrations are transmitted from the tool to the implant via the base plate, the same as shown in FIG. 4. After the implantation there are three ways of dealing with the tool.

Firstly, provided the opening in the bone tissue is a through-going opening, the tool is separated from the oscillation generator and removed towards the distal side. Secondly, the tool is also separated from the oscillation generator and remains with the implant, where it fulfils a predetermined function, e.g. serves for attaching a further item. Thirdly, the tool is dismantled after the implantation, e.g. the shaft 3.4 is separated from the base plate 3.5.

The following variants are conceivable:

The cross-sections of the opening in the bone tissue and of the implant are not circular.

The tool is removable as a whole toward the proximal side if the cross-sections of the recess 1.9 and of the base plate 3.5 are not circular and the base plate 3.5 is able to be moved through the recess 1.9 in one specific rotational position.

The implant is not necessarily conical. Thus e.g. the opening in the bone tissue can get narrower toward the proximal side. While providing such an opening is generally difficult, there may still be cases in which this is favored by natural circumstances.

It is also possible that the implant as well as the opening in the bone tissue are e.g. cylindrical, i.e. their cross-sections remain constant along their axes. Then the cross-section of the implant would be slightly larger than that of the opening in the bone tissue, so that the implant is held in the opening by a press-fit. The frictional force may be strong enough to act as counter force to the force coupled into the implant by the tool. Alternatively a counter-element can be used in this embodiment.

Figure 14B:
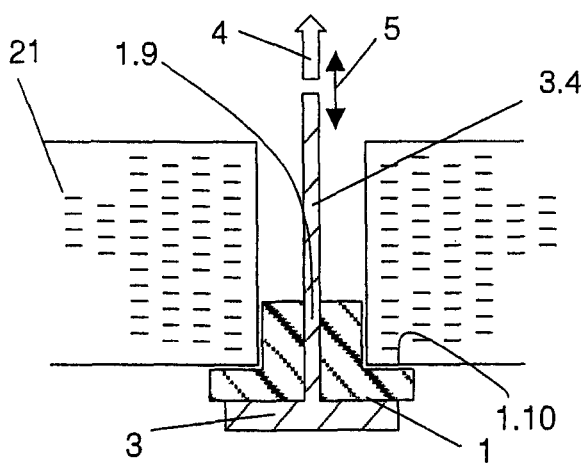

A further embodiment is illustrated in FIG. 14*b*. The implant 1 has a shoulder 1.10 being pressed against an equivalent shoulder of the bone tissue during implantation. In the illustrated case, the mouth of the opening forms the shoulder of the bone tissue, however it could also be designed as stepped or otherwise designed widening of the opening. FIG. 14*b* is a further example of an embodiment of the second aspect of the invention, in which the anchoring does not necessarily occur in the lateral walls of the opening.

Figure 15:
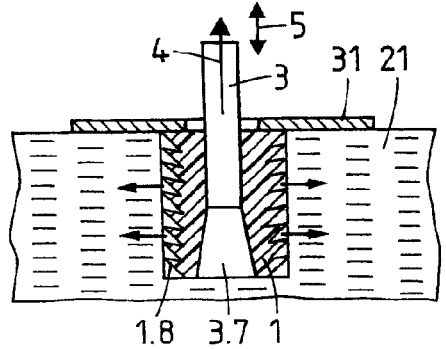
FIGS. 15 and 16 show embodiments of a combination of the second aspect and the third aspect of the invention.
Figure 16:
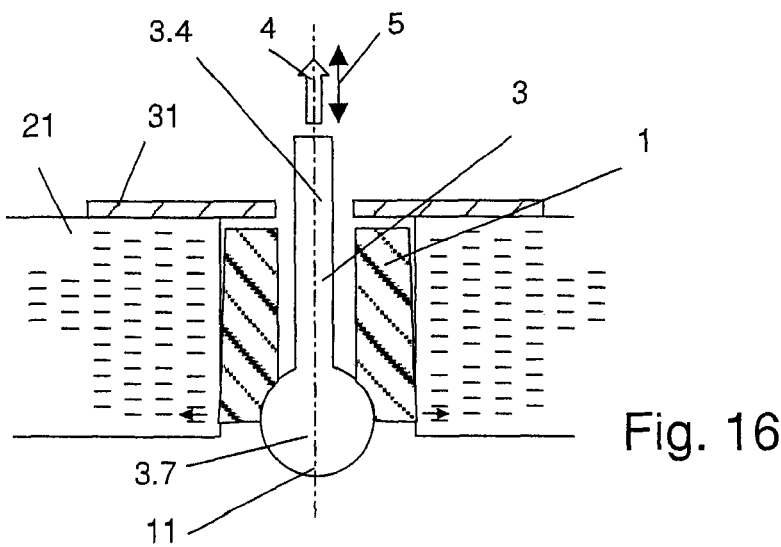
Figure 17:
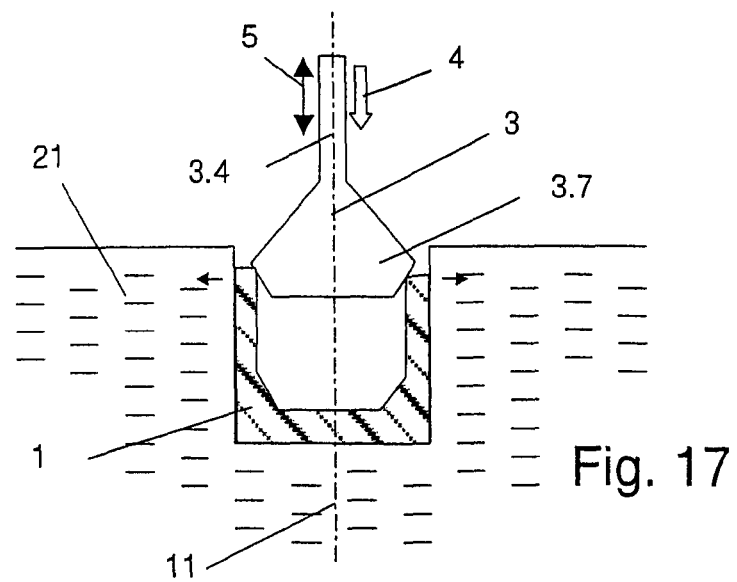
FIG. 17 illustrates a further embodiment according to the third aspect of the invention.

The following FIGS. 15 to 17 show embodiments according to the third aspect of the invention. The configurations in the examples according to FIGS. 15 and 16 correspond also with the second aspect of the invention.

In the configuration according to FIG. 15 a through-going or blind opening is provided in the bone tissue 21 in which the implant is introduced prior to the implantation. The implant 1 comprises a through-going or blind recess. The tool 3 comprises a shaft 3.4 (shaft portion) and a wedge 3.7 (distal end portion) tapering from the distal to the proximal side, where it is attached to the shaft. During implantation a pulling force 4 causes the wedge to be drawn through the recess of the implant 1 thereby expanding the latter. Thus a peripheral area of the implant is pressed against a lateral wall of the opening in the bone tissue. The mechanical vibrations, being coupled simultaneously into the implant, cause the thermoplastic material to liquefy where it is in contact with the bone tissue and to be pressed into cavities in the bone tissue. Advantageously the mechanical vibrations also cause the thermoplastic material to at least soften between the recess and the peripheral area. This softening leaves the implant free of tension after the removal of the tool, such preventing forces directed radially inwards acting on peripheral areas anchored in the bone tissue.

While the pulling force is exerted upon the tool a counter-element 31 prevents the implant from being drawn out of the opening. In the illustrated example, the implant 1 comprises peripheral, here pointed energy directors 1.8, which assist liquefaction of the liquefiable material. Energy directors can also be provided on implants according to other embodiments of the invention described in this document.

FIG. 16 shows an embodiment similar to the one of FIG. 15, wherein the tool is of a different shape. Instead of a wedge, the distal end portion of the tool is e.g. fashioned like a spherical swelling 3.7. During implantation this distal end portion is drawn through the implant while the thermoplastic material is liquefied and causes an advantageously plastic expansion of the implant as in the example according to FIG. 15.

Alternatively the tool may comprise instead of a shaft 3.4*a* a non-rigid element, e.g. a thread or a cable for pulling the distal end portion through the implant. The distal end portion may again be a spherical like in FIG. 16.

Further alternatives are conceivable:

A thickened distal end portion 3.7 of the tool can have many different shapes; the largest cross-section of the distal end portion must always be larger than the smallest cross-section of the recess in the implant and smaller than the cross-section of the opening in the bone tissue.

The recess of the implant 1 does not need to be through-going; moreover the tool can already be positioned in the recess designed as a blind hole prior to the implantation procedure and is then moved within or withdrawn from this recess during the implantation procedure. The advantage of such a configuration is the fact that the appropriate tool can be sold and stored together with the implant and the tool can also assist in positioning of the implant.

The opening in the bone tissue can either be through-going or blind.

A further object or a piece of tissue to be fixed to the bone tissue during the implantation process may be placed between the tool and the implant or between the implant and a lateral wall of the opening in the bone tissue. This also applies to the other embodiments according to the third or first aspect of the invention.

FIG. 17 shows a further embodiment according to the third aspect of the invention, wherein the force for expanding the implant during the implantation acts as compression load on the tool. While the distal end portion 3.7 of the implant in embodiments like the ones according to FIGS. 15 and 16 must comprise a component with a growing cross-section from the proximal to the distal side, in embodiments like the one according to FIG. 17, in which the tool is under compression load, a distal end portion with a growing cross-section from the distal to the proximal side is advantageous. In the illustrated example the distal end portion of the tool is designed like this.

For embodiments in which the force expanding the implant acts on the tool as compression load, the cross-sections of the shaft portion and of the distal end portion can be of equal size. The tool can be e.g. cylindrical, possibly tapering toward the distal side.

In the embodiment illustrated in FIG. 17 the implant is shaped like a cup and rests upon the bottom of the opening in the bone tissue. The implant can also be tubular or of another shape comprising a recess.

Figure 17A:
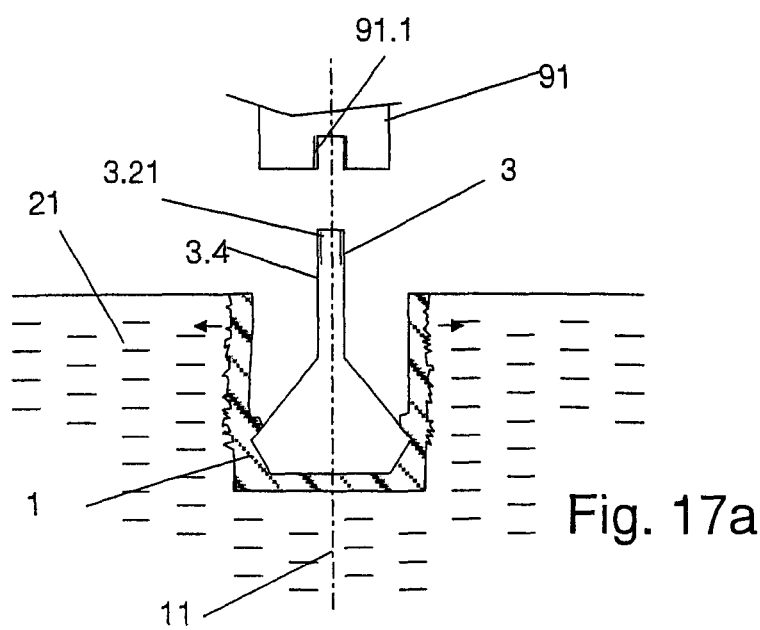
FIG. 17a shows the embodiment of FIG. 17 after implantation.

In the embodiment of FIG. 17, the tool 3 can be shaped so that it can be removed after implantation, for example if it narrows towards the distal side. As an alternative, the tool can be shaped so that it comprises a retaining structure (in the depicted embodiment formed by the shown shoulder) and itself serves as anchoring element after implantation. FIG. 17a depicts the tool 3 to comprise a threading 3.21 designed to co-operate with a threading of a further element 91, that may for example be an abutment of a dental implant, a dental implant itself, or a prosthesis etc.

The tool of the embodiment according to FIG. 11 has, in addition to the effect of compressing the implant, to some extent an expanding effect. The configuration according to FIG. 11 therefore corresponds to the first and the second aspect as well as to the third aspect of the invention.

Implants according to the third aspect of the invention are advantageously made entirely of the thermoplastic material. Non-thermoplastic components may be provided, e.g. at the base of a cup-shaped implant, at the periphery of an area where no expansion is desired, or as a reinforcing element designed and situated not to obstruct the expansion. In the case of a tube- or cup-shaped implant such reinforcements can e.g. be of an elongated shape and extend spread out on the circumferential surface of the implant in axial direction.

In all embodiments according to the first and the third aspect of the invention, the opening (if present) in the implant does not need to be central. A corresponding asymmetrical configuration can be used in order to specifically liquefy or plastify the thermoplastic material on one implant side earlier than on the opposite side, or it may be intended that the thermoplastic material only liquefies or plastifies on one side.

Figure 18:
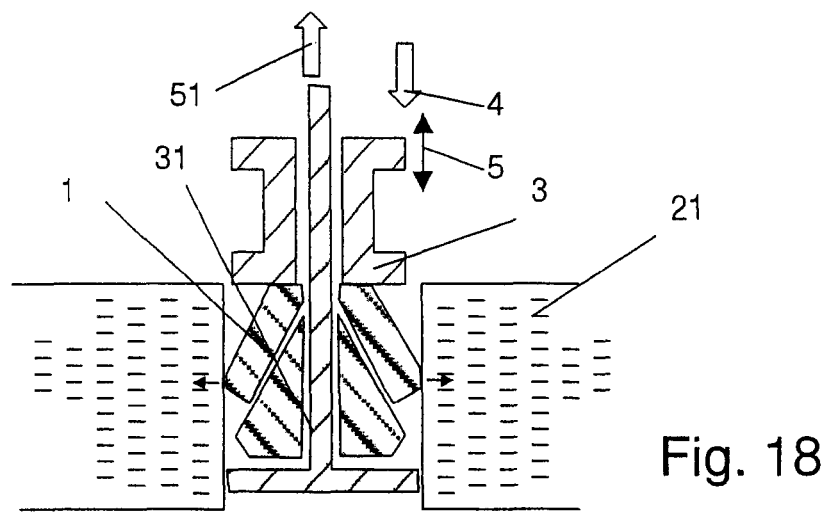
FIG. 18 illustrates the principle of a distal counter-element.

Also in cases, where the tool is under compression force, a counter-element 31 can be applied. Such an element acts on the distal side of the implant and is e.g. held by a shaft extending centrally through the tool, as illustrated in FIG. 18, which shows an example according to the first aspect of the invention. In such cases, it is not necessary for embodiments according to the first aspect of the invention that the tool 3 is moved when force 4 is coupled into it. Instead, the counter-element 31 coupling the counterforce 51 into the implant can be moved during the implantation procedure. Combined motions of the tool and the counter-element are also possible. It is further possible that the counter-element 31 is designed as a tool and therefore also couples mechanical vibrations into the implant, i.e. the mechanical vibrations are coupled into the implant from two sides.

Figure 19:
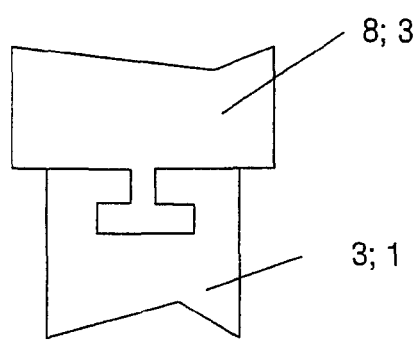
FIG. 19 shows a coupling suitable for transmission of a pulling force.

In all embodiments designed according to the second aspect of the invention the force 4 to be coupled into the implant acts a tensile force on the tool 3 or (as in configurations according to FIG. 18) if necessary on the counter-element 31. This requires an appropriate coupling means on the vibratory device, which does not only need to be suitable for tensile force but also for the transmission of mechanical vibrations while under tensile force. Such coupling means are known to someone skilled in the art. They are often based on a form fit (screw joints, snap fastenings, bayonet catches, etc.) or possibly a material fit (glued, welded or soldered connections) or a friction fit (clamped connections). Such generally known coupling means are not further discussed here. The principle of a form-fit coupling means is shown in FIG. 19. This coupling can be used as shown or in an alternative form. The vibratory device comprises an extension protruding into a clearance at the proximal end of the tool 3 and widening towards its distal end so that it can transmit a tensile force. For coupling the tool 3 to the vibratory device, these are moved perpendicular to the plane of FIG. 19 relative to each other. Dovetails or similar modifications may be considered. In embodiments such as shown in FIG. 13 these or other coupling means can also be used to transmit tensile forces from the tool 3 to the implant 1.

Figure 20:
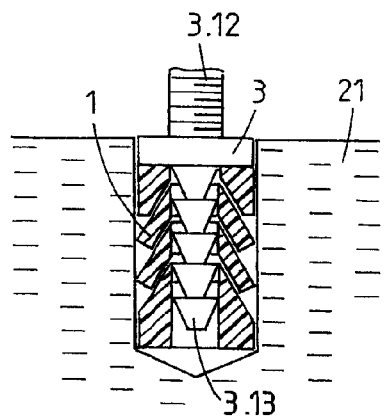
FIG. 20 illustrates yet a further variant of an implant and method according to the first aspect of the invention.

In embodiments where the tool 3 remains in place after implantation, the tool often is provided with a distal portion with a larger cross section, said distal portion being arranged distal of a main portion of the implant (c.f. FIG. 4, FIG. 20.). In embodiments where the necessary force is applied to the tool as a compressive force, this is often not an option, as the tool there is moved "forward", i.e. towards a distal side during implantation. FIG. 20 illustrates an embodiment of such "forward" implantation, where the tool 3 may nevertheless remain in the place of the implantation after implantation. To this end, the tool is provided with retaining structures 3.13 that cause the tool to be retained by the implant 1 after implantation. In FIG. 20, also a thread 3.12 of the tool is illustrated that may be used to fix some other object to the implant.

Figure 21A:
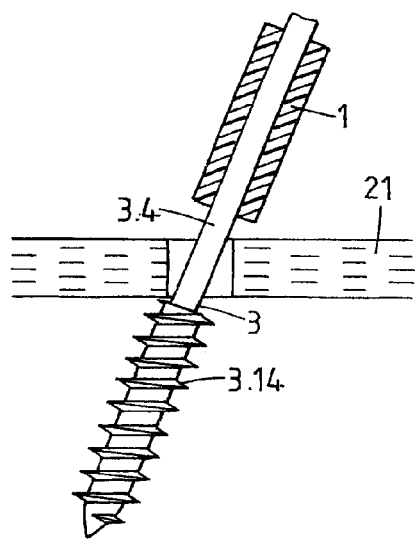
FIGS. 21a and 21b show yet another embodiment of the invention.
Figure 21B:
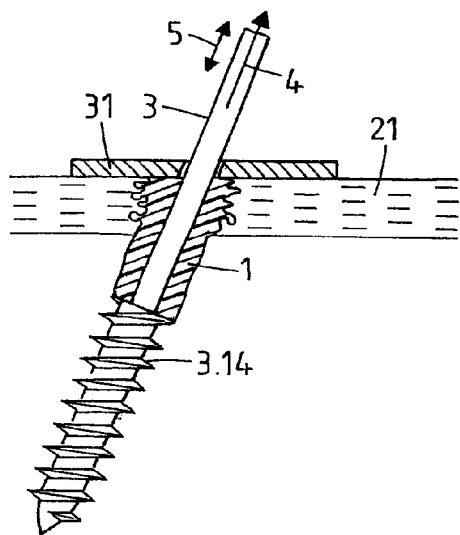

FIGS. 21a and 21b illustrate another embodiment of the second aspect of the invention that is especially suited for affixing the implant to cortical bone. The tool 3 is provided with reaming structures 3.14 with a larger external diameter than the shaft 3.4. The tool is first used to drill a hole into the cortical bone by means of the reaming structures. Thereafter, the tube shaped implant 1 is pushed on the shaft. The external and internal diameters of the implant 1 are such that it can pass through the hole, but abuts the reaming structures 3.14. For implanting, the implant is pressed against the counter element 31 by pulling the tool 3, the implant being compressed between the tool and the counter element. The liquefiable material liquefies in contact with the cortical bone material, and since this bone material is very hard with little porosity, it may ooze out on the distal side of the corticalis, form a bulge, and thereby act in a blind rivet like manner.

Instead of the tool comprising the reaming structures, it may also comprise a distal enlargement by which the force may act on the tool, and the hole in the corticalis may then be drilled by an instrument different from the tool.

Figure 22A:
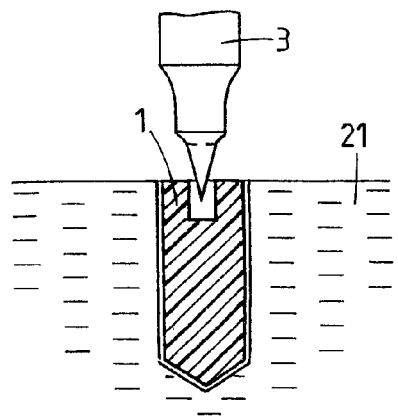
FIGS. 22a and 22b show a further embodiment of the third aspect of the invention.
Figure 22B:
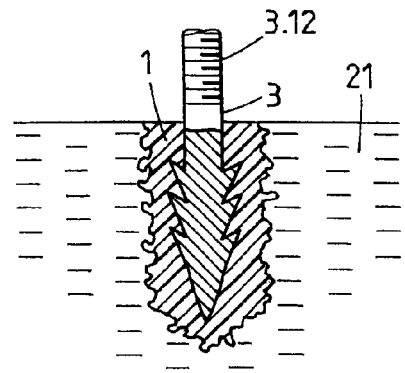

Referring to FIGS. 22*a* and 22*b*, 23*a*, 23*b*, and 24, further examples of the third aspect of the invention are described. The embodiments of implants 1 shown therein comprise an implant section (in both depicted embodiments the implants consist of said section) consisting of a thermoplastic material, where during implantation a distal portion of the tool 3 protrudes into an interior of said section and during implantation spreads the implant section from an inside. This results in lateral forces onto the interfaces between the implant and the hard tissue or hard tissue replacement material surface, thereby improving anchoring in lateral walls of the tissue/tissue replacement material. The depicted embodiments show two possibilities to spread the implant, by the tool, from the inside:

The tool 3 is driven into the implant during implantation, thereby enlarging an outer cross section (FIGS. 22*a*, 22*b*). The tool in the shown embodiment comprises barb-like structures for the tool being kept fixedly in the implant after implantation.

Figure 23A:
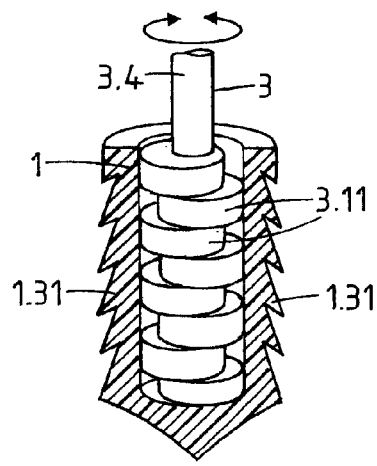
FIGS. 23a and 23b show yet another embodiment of the third aspect of the invention.
Figure 24:
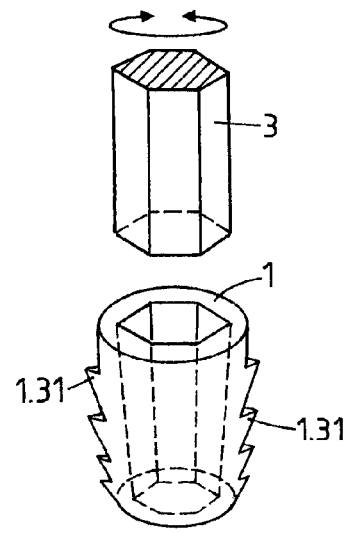
FIG. 24 shows a variant of the embodiment of FIGS. 23a and 23b.
Figure 23B:
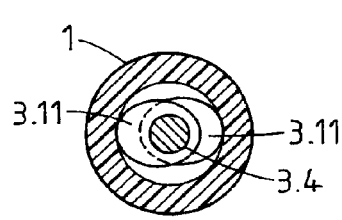

The tool is not rotationally symmetric and is rotated during implantation, while rotation of the implant is inhibited (FIGS. 23, 23*b*, 24). In FIGS. 23*a*, 23*b*, the tool comprises a plurality of eccentrics 3.11, whereas in FIG. 24 both the tool and the opening in the implant are translation symmetric but not rotational symmetric, and are, in the illustrated embodiment, hexagonal in cross section. The depicted implants 1 comprise barb like protrusions 1.31 inhibiting rotation.

The methods and implants described in this text may be used for a broad variety of surgical applications. For example, implants according to the invention may be used in almost any applications where hitherto screws or anchors were placed in bone; this includes the fixation of fractures or distractions by pin like implants, the fixation of prostheses by expanding stem like elements in the cancellous bone or in the intermedullary canal, an approach that could also be used to achieve distal and proximal locking of intermedullary nails, the fastening of plates, membranes or meshes with the aid of pin like implants using this embodiment, the fastening of ligaments or tendons by suture anchors especially in thinner bone structures, the fastening of webs etc. the expansion principle is suitable to achieve anchoring in osseous membranes, implants for cranial and maxillofacial surgery or for fixation in the shoulder blade, Sternum (closure of osteotomies) (U.S. application Ser. No. 11/694, 249 being incorporated herein by reference shows some examples with specially designed implants).

Some of the new applications of implants are described in this text. These applications described herein are mere examples of new uses the approach according to the invention makes possible, the new applications being by no means restricted to the described examples.

FIGS. 25*a* and 25*b* show, in a generic way, how implants according to the invention may be used in the place of a state of the art compression or lag screw used to press one hard tissue part against another hard tissue part. The implant 1 comprises an implant portion (in the pictured embodiment being the distal implant portion) corresponding to the first and/or second aspect of the invention; for example being configured as depicted in FIG. 3*a*/FIG. 4. This distal implant portion is anchored in a first, distal bone fragment 21.1 by the method described referring to FIG. 4, the implant shaft 1.24 thereby serves as the counter element (FIG. 25*a*). Thereafter, optionally a proximal portion of the tool 3 is removed, and a proximal portion of the implant is at least partially plastified or liquefied to form an implant head and/or to interpenetrate structures of the surfaceing bone material of a second, outer bone fragment 21.2 (FIG. 25*b*) or standard counter-locking elements as formed heads, plates and meshes are used.

The implant shaft 1.24 in this embodiment may consist of the thermoplastic material liquefieable by mechanical oscillations, or it may comprise material portions of non-liquefiable material.

In FIG. 26 an example of resurfacing of a joint by means of an implant and a method according to the invention is illustrated. The depicted bone 21 is a femur, of which the femoral head or a cup like structure acting as a resurfacing prosthesis replacing primarily the destroyed cartilage layer but sparing most of the underlying bone structure is replaced. This is shown here for a femoral head resurfacing prostheses, comparable approaches can be used for almost all joints in the human skeleton, being convex, concave, flat or of multicurvature geometry. The tool 3 is fastened in a bore in the femur by means of the joint use of the methods according to the first and second aspect of the invention as illustrated in FIG. 11 (as an alternative, other embodiments of the method according to the invention could be used, for example the embodiment depicted in FIG. 4, or the embodiment shown in FIG. 17*a* etc.). The shaft 3.4 of the tool 3 serves as anchor for fastening the resurfacing prosthetic element 102. Depending on the joint, several tools 3 might be inserted to allow for a multipoint-anchoring of the element 102.

Of course, various other embodiments of implants can be envisaged.

Implants, devices and implantation methods according to the illustrated or other embodiments of all aspects of the invention find their use in various situations where a firm connection between the implant and the bone tissue is important. For anchoring implants in osteoporotic bone tissue and for other specific applications reference is made to all applications as described in the publications WO 02/069 817, WO 2004/017 857 and WO 2005/079 696, whose contents are incorporated herein by reference.

What is claimed is:

1. An implant suitable for being anchored with the aid of mechanical vibration in an opening in bone tissue or other hard tissue, the implant defining an axis and the implant further comprising a coupling-in face for applying a compressing force and the mechanical vibration, said coupling-in face being not parallel to the axis, the implant comprising at least two implant components, the implant components being configured and arranged to be pressed against each other along a common contact interface when a compressing force acts on the implant along the axis and to thereby undergo a relative shifting movement along the common contact interface, wherein the implant further comprises a thermoplastic material forming at least a part of a peripheral surface portion, and wherein the compressing force applied along the axis causes an enlargement of a distance between the peripheral surface portion of the implant and the compression axis when the thermoplastic material is in a solid state.

2. The implant according to claim 1, wherein the common contact interface extends obliquely to the axis.

3. The implant according to claim 2, wherein the common contact interface is conical.

4. The implant according to claim 1, wherein the compressing force causes at least one of the components to be spread.

5. The implant according to claim 1, wherein the coupling-in face is at least partly even and oriented perpendicular to the compression axis.

6. The implant according to claim 1, wherein the implant components, prior to implantation, are separate or linked via predetermined breaking or melting points.

7. The implant according to claim 1, wherein surfaces of the implant components consist of thermoplastic material at least to the extent that the implant components are able to be welded together by the effect of the mechanical vibrations and the compressing force.

8. An implant suitable for being anchored with the aid of mechanical vibrations in an opening in bone tissue or other hard tissue, the implant extending along an axis between a proximal end face and a distal end face, wherein the implant comprises a plurality of components, one of the components comprising the proximal end face and another one of the components comprising the distal end face, wherein a peripheral surface portion of the implant comprises a thermoplastic material, wherein the components are configured and arranged relative to one another so that when the implant is compressed by a compressing force between the proximal and distal end faces while the thermoplastic material is in a solid state, the peripheral, surface portion is pressed outwardly away from the axis, whereby the implant is capable of being anchored in the opening in the bone tissue or other hard tissue by applying the compressing force and by coupling mechanical vibration into the implant via the proximal end face or the distal end face or both, and by thereby pressing the peripheral surface portion against a lateral wall of the opening and at least partially liquefying the thermoplastic material where in contact with the lateral wall and pressing the liquefied thermoplastic material into structures of the bone tissue or other hard tissue to form, after re-solidification, a positive fit connection with the lateral walls.

9. The implant according to claim 8, wherein the components are designed to be shifted relative to each other by the compressing force along shifting surfaces extending obliquely to the compression axis.

10. The implant according to claim 8, wherein the compressing force causes at least one of the components to be spread.

11. The implant according to claim 8, wherein the components are weldable to each other.

12. The implant according to claim 8, wherein at least one of the components essentially has a shape of a hollow cone or hollow truncated cone.

13. The implant according to claim 8, wherein at least one common contact interface between the components has a shape of a lateral surface of a truncated cone.

* * * * *